US011633123B2

United States Patent
Saalbach et al.

(10) Patent No.: US 11,633,123 B2
(45) Date of Patent: Apr. 25, 2023

(54) MOTION ARTIFACT PREDICTION DURING DATA ACQUISITION

(71) Applicant: KONINKLIJKE PHILIPS N.V., Eindhoven (NL)

(72) Inventors: Axel Saalbach, Hamburg (DE); Steffen Weiss, Hamburg (DE); Karsten Sommer, Hamburg (DE); Christophe Schuelke, Hamburg (DE); Michael Helle, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 203 days.

(21) Appl. No.: 16/759,755

(22) PCT Filed: Oct. 26, 2018

(86) PCT No.: PCT/EP2018/079378
§ 371 (c)(1),
(2) Date: Apr. 28, 2020

(87) PCT Pub. No.: WO2019/086337
PCT Pub. Date: May 9, 2019

(65) Prior Publication Data
US 2021/0177296 A1    Jun. 17, 2021

(30) Foreign Application Priority Data

Oct. 31, 2017  (EP) ..................................... 17199301
Apr. 30, 2018  (EP) ..................................... 18170128

(51) Int. Cl.
*A61B 5/055* (2006.01)
*G16H 30/40* (2018.01)
*A61B 5/00* (2006.01)

(52) U.S. Cl.
CPC ............ *A61B 5/055* (2013.01); *A61B 5/7207* (2013.01); *A61B 5/7267* (2013.01); *G16H 30/40* (2018.01)

(58) Field of Classification Search
CPC ...................................................... A61B 5/055
See application file for complete search history.

(56) References Cited

U.S. PATENT DOCUMENTS

2017/0365047 A1    12/2017   Beque et al.
2017/0372155 A1    12/2017   Odry et al.

FOREIGN PATENT DOCUMENTS

WO        2019086284 A1     5/2019

OTHER PUBLICATIONS

Kustner et al., Automated reference-free detection of motion artifacts in resonance images, Sep. 2017, Magnetic Resonance Materials in Physics, Biology and Medicine, 31, 243-256 (Year: 2017).*

(Continued)

*Primary Examiner* — Joseph M Santos Rodriguez
*Assistant Examiner* — Maria Christina Talty

(57) ABSTRACT

A magnetic resonance imaging system including a memory configured to store machine executable instructions, pulse sequence commands, and a first machine learning model including a first deep learning network. The pulse sequence commands are configured for controlling the magnetic resonance imaging system to acquire a set of magnetic resonance imaging data. The first machine learning model includes a first input and a first output, a processor, wherein execution of the machine executable instructions causes the processor to control the magnetic resonance imaging system to repeatedly perform an acquisition and analysis process including: acquiring a dataset including a subset of the set of magnetic resonance imaging data from an imaging zone of the magnetic resonance imaging system according to the pulse (Continued)

sequence commands, providing the dataset to the first input of the first machine learning model, in response to the providing, receiving a prediction of a motion artifact level of the acquired magnetic resonance imaging data from the first output of the first machine learning model, the motion artifact level characterizing a number and/or extent of motion artifacts present in the acquired magnetic resonance imaging data.

20 Claims, 16 Drawing Sheets

(56) References Cited

OTHER PUBLICATIONS

Thomas Küstner et al. "Automated reference-free detection of motion artifacts in magnetic resonance images" Magnetic Resonance Materials in Physics, Biology and Medicine (MAGMA), vol. 31, No. 2, Sep. 20, 2017, pp. 243-256.
Kristof Meding et al "Automatic detection of motion artifacts in MR images using CNNS", 2017 IEEE International Conference on Acoustics, Speech and Signal Processing (ICASSP), Mar. 5, 2017, pp. 811-815.
International Search Report and Written Opinion from PCT/EP2018/079378 dated Jan. 28, 2019.

* cited by examiner

MOTION ARTIFACT PREDICTION DURING DATA ACQUISITION

CROSS REFERENCE TO RELATED APPLICATIONS

This application is a U.S. national phase application of International Application No. PCT/EP2018/079378 filed on Oct. 26, 2018, which claims the benefit of EP Application Serial No. 17199301.7 filed on Oct. 31, 2017 and EP Application Serial No. 18170128.5 filed Apr. 30, 2018 and is incorporated herein by reference.

FIELD OF THE INVENTION

The invention relates to processing motion artifacts in magnetic resonance imaging data, in particular it relates to predicting motion artifacts during magnetic resonance imaging data acquisition.

BACKGROUND OF THE INVENTION

Due to typically long data acquisition times of magnetic resonance imaging (MRI) procedures, motion artifacts caused by patient motion are one of the most frequent causes of image degradation of magnetic resonance images in clinical applications of MRI. Possible problems associated with motion artifacts may for example comprise that the respective magnetic resonance images may be of little or even no use for medical diagnosis due to the image degradation. Such a degraded magnetic resonance image may require a complete repetition of the magnetic resonance imaging procedure.

SUMMARY OF THE INVENTION

The invention provides for a magnetic resonance imaging data processing system, a method of operating the magnetic resonance imaging data processing system, and a computer program product in the independent claims. The invention further provides a magnetic resonance imaging system comprising the magnetic resonance imaging data processing system. Embodiments are given in the dependent claims.

In one aspect, the invention relates to a magnetic resonance imaging system. The magnetic resonance imaging system comprises a memory storing machine executable instructions, pulse sequence commands and a first machine learning model comprising a first deep learning network.

The pulse sequence commands are configured for controlling the magnetic resonance imaging system to acquire a set of magnetic resonance imaging data. The first machine learning model comprises a first input and a first output.

The magnetic resonance imaging system further comprises a processor. An execution of the machine executable instructions causes the processor to control the magnetic resonance imaging system to repeatedly perform an acquisition and analysis process. The respective process comprises acquiring a dataset comprising a subset of the set of magnetic resonance imaging data from an imaging zone of the magnetic resonance imaging system according to the pulse sequence commands. The dataset is provided to the first input of the first machine learning model. In response of the providing of the dataset to the first input, a prediction of a motion artifact level of the acquired magnetic resonance imaging data is received from the first output of the first machine learning model. The motion artifact level characterizes a number and/or extent of motion artifacts present in the acquired magnetic resonance imaging data.

Embodiments may have the beneficial effect of enabling to monitor the motion artifact level of MRI dataset during the acquisition of the MRI data. The quality of the acquired MRI data may thus be monitored throughout the acquisition process. In case problems occur regarding the motion artifacts, the same can be handled at an early stage. Embodiments may have the beneficial effect that they are not limited to a retrospective quality assessment of the acquired magnetic resonance data after the acquisition has been completed anymore. For example, a re-start of a time-consuming data acquisition process may be started at a very early stage, if artifacts are detected during the data acquisition.

According to embodiments, the magnetic resonance imaging system is provided with access to a machine learning model configured for deep learning-based motion artifact detection during MRI data acquisition. The acquisition of the magnetic resonance imaging data to be acquired according to the pulse sequence commands may be split up into an acquisition of a plurality of datasets, each comprising a subset of the magnetic resonance data to be acquired.

The first machine learning model is trained, i.e. configured, for detecting the presence of motion artifacts in MRI datasets received via the first input, determining a prediction of a motion artifact level based on the detected motion artifacts present in the received MRI data. The resulting prediction is provided in reply to the received MRI data via the first output. The predicted motion artifact level characterizes the number and/or extent of the motion artifacts detected in the MRI data received via the first input.

Image degradation of magnetic resonance images due to subject motion during the acquisition of magnetic resonance data is one of the most persistent problems in the clinical application of magnetic resonance imaging. The associated motion artifacts may e.g. be a result of long acquisition times and may e.g. appear as ghosting or blurring in the images. Low quality images may have a negative impact on subsequent diagnostic as well as therapeutic process. Motion artifacts may reduce image quality to a degree that makes medical analysis impossible. Furthermore, they may also have a negative impact the overall clinical workflow, e.g. when the MRI data acquisition has to be repeated after it has already been completed. For example, artifacts may result in misdiagnosis, e.g. by obscuring the presence of lesions, or may require a repetition of the scan comprising the entire MRI data acquisition process.

Known methods for artifact detection are developed for a retrospective quality assessment of magnetic resonance data for which the acquisition process is already completed. Using such a retrospective approach, imaging problems may remain undetected until a scan has been completed. As artifacts may be caused by events or conditions throughout the acquisition process, techniques for an early detection as well as corresponding mitigation strategies may be beneficial.

According to embodiments, the prediction of the artifact level may be used as a quality indicator which is displayed on a display during data acquisition. Furthermore, after the MRI data acquisition is completed, the final prediction of the artifact level may be assigned to the acquired set of MRI data.

In the presence of severe artifacts, embodiments may enable a technician supervising the MRI data acquisition to abort the acquisition process at an early stage and to address the cause of the problem. For example, the patient may be provided with instructions. The splitting of the MRI data acquisition and analysis process in a plurality of repetition loops, with each repetition handling a subset of the set of magnetic resonance imaging data to be acquired according to the pulse sequence commands, enables detecting of inconsistencies between datasets, identifying potential isolated motion artifacts. An isolated motion artifact refers to a motion artifact that is limited to one or more succeeding datasets. In case the subject, from which the magnetic resonance imaging data is acquired, moves out of an initial position and returns into the initial position, the resulting motion artifact may be limited to those magnetic resonance data only which is acquired during the movement. This motion-artifact-corrupted magnetic resonance data may be determined and omitted. Alternatively, the motion-artifact-corrupted magnetic resonance data may be processed in order to correct the motion artifact.

Embodiments may have the beneficial effect of improving workflow efficiency as well as image quality. On the one hand it may be avoided that a time-consuming acquisition of the entire set of magnetic resonance data is executed even though the acquisition suffers from motion artifacts. Embodiments may rather enable aborting the data acquisition on an early stage. On the other hand, it may be ensured that the acquired magnetic resonance data satisfies predefined quality standards, e.g. in form of a maximum artifact level. In case the maximum artifact level is exceeded, the acquired magnetic resonance data may be discarded.

According to embodiments, the acquisition of the datasets may be executed continuously, i.e. immediately after the acquisition of a dataset is finished, the acquisition of the next dataset may be started. In other words, the repetitions of the acquisition and analysis process may overlap each other, i.e. while an acquired dataset is provided to the first input of the first machine learning model, acquisition of the next dataset may have started.

According to embodiments, the acquisition of the datasets may be executed discontinuously, i.e. in discrete steps, wherein a repetition of the acquisition and analysis process has to be finished before the next repetition and thus, the acquisition of the next dataset is started.

The MRI data comprised by the MRI dataset provided to the first input of the first machine learning input may be provided in k-space or image space representation.

According to embodiments, the deep learning network is a deep convolutional neural network implementing deep learning. Embodiments may have the beneficial effect that a deep convolutional neural network may be well suited for predicting motion artifact levels MRI datasets. According to embodiments, deep learning techniques, e.g. convolutional neural networks (CNN), are deployed for motion artifact detection and prediction of an artifact level. Given a set of annotated training sets, a CNN may be optimized such that it is enabled to classify MRI datasets with respect to predefined category levels, like e.g. from "no artifact" to "severe artifact", or to assign a continuous quality score.

Embodiments may have the beneficial effect of providing an automatic processing of motion-related artifacts in magnetic resonance images using deep learning implemented by a deep learning network during data acquisition. The deep learning network may e.g. be implemented in form of a deep convolution neural network or a fully convolutional network. Embodiments may facilitate a robust and reliable processing of motion artifacts. Processing of motion artifacts may further enable determining the impact of the same on the image quality without requiring any user interaction. Furthermore, e.g. in case of a filtering of the motion artifacts, their impact on the image quality may be minimized, i.e. reduced or even canceled. Embodiments may for example be implemented for a fast processing of MRI datasets already during data acquisition, e.g. as part of a magnetic resonance imaging system, in course of a control of the acquisition of a set of MRI data comprising a plurality of subsets in form of MRI datasets.

A large number of methods has been developed to avoid the appearance of motion artifacts in magnetic resonance images, such as faster imaging techniques, motion correction using either navigators or external tracking devices. Motion correction can be performed either prospectively, i.e. by adjusting the scan parameters during the scan, or retrospectively, i.e. by modifying the collected data. However, known approaches for motion artifact reduction may either complicate the clinical workflow, such as methods that involve mounting a tracking device on the subject, or may only be applicable to particular imaging situations, such as navigator-based approaches that require additional scan time.

Embodiments may overcome these problems by adopting a deep-learning-based approach to correct for motion artifacts in MRI datasets and in particular in MRI images.

Embodiments may facilitate automatic detection of motion-related artifacts in MRI data and, e.g. based on the application of a tailored deep convolutional neural network, provide a prediction of a current artifact level during data acquisition without requiring any user input.

The trained deep learning network provided by the first machine learning model, e.g. in form of a deep convolutional neural network, may implement an effective automatic notification system for motion artifacts during MRI data acquisition. In case motion artifacts are in the MRI data acquired, the user may be notified at an early stage about the presence of motion artifacts in form of the prediction of the motion artifact level. Thus, the user may be enabled to take adequate measures and/or conclusions based on the respective notification. For example, magnetic resonance data acquisition may be aborted, (partially) repeated, the patient may be repositioned and/or instructed in order to avoid further motion artifacts.

The motion artifact level may range from motion-artifact-free, rendering the imaging datasets, more particular MRI images, well suited for diagnosis, to heavily motion-artifact-corrupted, rendering the respective images inadequate for diagnosis.

The motion artifact level may for example be provided in form of a quantitative label describing the level of motion artifacts present in the MRI data. According to embodiments, the prediction of the motion artifact level may be received in form of continuous quantity, like e.g. a real-valued quantity. This real-valued quantity may e.g. be calculated using regression.

According to embodiments, the first machine learning model classifies motion artifacts comprised by the MRI data provided to the first input by assigning a prediction of the motion artifact level to the respective data. The trained deep learning network may classify the motion artifact level(s), i.e. determine to which class of a set of classes (categories) the received MRI data belongs. Such a classification may be considered as a specific type of pattern recognition. Classification is an instance of supervised learning. The motion artifact level may be provided in form of a discrete motion artifact level identifier, like e.g. a categorical (e.g. "A", "B", "C", . . . ), ordinal (e.g. "low", "medium", "high", . . . ) or integer-valued ("0", "1", "2", . . . ) quantity identifying the determined motion artifact level.

According to embodiments, the motion artifact level may be provided in form of a continuous motion artifact level identifier, like e.g. a real-valued quantity. This real-valued motion artifact level identifier may e.g. be calculated using regression.

Thus, in case of a motion artifact level determination, the trained deep learning network may receive the magnetic resonance imaging datasets as input and return a single quantity, i.e. the motion artifact level, as output.

According to embodiments, the execution of the machine executable instructions further causes the processor to control the magnetic resonance imaging system to automatically abort the repeated performing of the acquisition and analysis process, if the prediction of the motion artifact level exceeds a first predefined threshold.

The first threshold may define a maximum value of the motion artifact level at which the respective MRI data is still usable. In case the first threshold is exceeded, there may be a high probability that the corruption of the respective MRI data is server such that they are e.g. not suitable for diagnostic purposes anymore.

According to embodiments, the execution of the machine executable instructions further causes the processor to control the magnetic resonance imaging system to automatically restart the repeated performing of the acquisition and analysis process, if the prediction of the motion artifact level exceeds the first predefined threshold.

Upon identification of motion-artifact-corrupted MRI data, the magnetic resonance imaging system is configured to decide upon performing a re-scan. In case magnetic resonance imaging data acquired is identified to be motion-artifact corrupted, e.g. due to a sudden movement, an automatic re-scan may be initiated. Thus, the prediction of the artifact level may be used to trigger an automatic re-scan of the affected data.

According to embodiments, the predicted motion artifact level depends on the location of the artifacts relative to one or more anatomical structures of interest represented by the acquired magnetic resonance data. Embodiments may have the beneficial effect that as long as the representation of the anatomical structures which are to be assessed using the acquired magnetic resonance data is not influenced by the motion artifacts additional scans or processing steps may be avoided.

According to embodiments, each of the datasets comprises a magnetic resonance image reconstructed using the acquired magnetic resonance data. Each of the datasets may e.g. a 2D image corresponding to a 2D slice through the imaging zone.

According to embodiments, each of the datasets comprises acquired magnetic resonance imaging data corresponding to one or more individual two-dimensional slices through the imaging zone.

An MRI scan may involve a stack of parallel oriented 2D slices, that are acquired and reconstructed sequentially, also referred to as multi-2D mode. In a multi-2D mode, the MRI data may be acquired slice by slice. In other words, a 2D slice of the imaging volume is excited and MRI data of this excited plane is acquired. By repeating this excitation and acquisition for multiple parallel slices, the stack of 2D slices may be generated which resembles the 3D imaging volume. Each MRI dataset may e.g. comprise a single 2D-slice. Thus, for each slice, an individual repetition of the data acquisition and analysis process may be executed.

The MRI data may be provided to the first machine learning model in form of k-space data or in form of a reconstructed magnetic resonance image. For example, for each individual slice an individual image may be reconstructed and analyzed, while data acquisition for consecutive slices still continues. For each of the slices an individual artifact level may be predicted using the first machine learning model.

Embodiments may allow for monitoring and estimating the image quality of the stack of 2D slices. The image quality may e.g. be estimated in form of the largest artifact level predicted for one of the slices or as an average of the artifact levels predicted for the slices. The respective quality estimate may be displayed/indicated in terms of textual information, graphical information, like e.g. traffic lights, or by means of acoustic signals.

It is also proposed to display the current ratio of artifact-corrupted slice and/or the probability that the scan must be repeated. In combination with a survey scan, also spatial occurrence of artifacts can be displayed (e.g. in order to let the technician avoid the abortion of a scan if motion occurs only in less sensitive areas of the image stack).

An MRI scan may involve a 3D volume, referred to as a 3D-mode, wherein the full imaging volume is excited and MRI data is acquired from sampling points distributed over the full 3D volume. Thus, all the acquired MRI data is required to reconstruct the 3D volume. In order to generate a suitable representation of the acquired 3D MRI data, image processing may be used to create 2D images representing slices through that 3D volume or to create a 3D image.

For the 3D-mode, a different approach compared to the multi-2D-mode may be required. 3D MRI scans may already have some means to account for expected repetitive physiological motion such as respiratory or cardiac motion, if this is mandated by the anatomical structure of interest to be scanned and/or by a known sensitivity of the scan method used to such motion. Examples for such motion accounting means are respiratory or cardiac gating and triggering. However, these may not account for types of motion that are non-repetitive, i.e., types of motion, where the patient lies relatively still for a long time and suddenly moves, e.g. due to coughing or to relieve an uncomfortable position.

Such non-repetitive or not necessarily repetitive motions have another property that may be exploited for motion artifact correction, namely sparsity in time. Sparsity in time of such motions may result in two different forms of k-space inconsistency. If the patient after the motion returns to the original posture, only a portion of 3D k-space data becomes corrupted. If the patient after the motion remains in a new posture, k-space becomes divided into two parts that are consistent within themselves but inconsistent with each other. This fact and the knowledge of the k-space trajectory, i.e. the time order of data sampling and thus data filling into k-space may be used to continuously assess image quality with respect to motion artifacts during data acquisition.

According to embodiments, in each repetition the dataset acquired during the respective repetition is provided to the first input in combination with the datasets acquired in all the repetitions preceding the respective repetition. Embodiments may have the beneficial effect that problems regarding the detection and classification of motion artifacts due to undersampling, i.e. a too small number of sampling points for an accurate image reconstruction may be avoided.

According to embodiments, k-space may be subdivided into n datasets with n chosen such that each dataset contains a relevant chunk of data, e.g. 5<n<10. Each dataset comprises MRI data from sampling points of a segment of k-space. The datasets are acquired successively, each over a time segment. As soon as the MRI data of a time period $P_i$ is fully acquired, a 3D image $Im_i$ may be reconstructed using the acquired from all time periods $P_k$ with $k \leq i$, i.e. all acquired MRI data available at this point of time. The resulting image may typically result in an image with reduced resolution compared to an image reconstructed from the MRI data of the full 3D scan, i.e. from the MRI data of all the n datasets.

The image $Im_i$ may be subjected to the motion classifier provided by the first machine learning resulting in a prediction of a motion level $L_i$. If $L_i > L_{i-1}$, i.e. if the artifact level increases due to including the latest dataset of time period $P_i$, then it is likely that the patient has moved during the respective time period $P_i$. According to embodiments, the increase may be indicated. According to embodiments, it may be checked, whether the inclusion of the MRI data acquired during the following time period $P_{i+1}$ instead of the MRI data of time period $P_i$ also results in an increased artifact level. In other words, a reduced image $rIm_{i+1}$ is reconstructed taking into account MRI data from all time periods $P_k$ with $k \leq i+1$ except of $k=1$. In other words, the MRI data from time period $P_i$ is omitted.

In case, an omission of the MRI data from time period $P_i$ results in an increase of the prediction for the motion level $L_{i+1}$ relative to the prediction for $L_{i-1}$, the patient may have reached a new posture. Therefore, the MRI scan should be terminated and restarted. In the other case, the motion of the patient may be restricted to time period $P_i$ and the patient may have returned to the original posture. Therefore, re-acquisition of MRI data of time period $P_i$ may be performed as a replacement of the motion-artifact-corrupted MRI data previously acquired in time period $P_i$.

It may be required to limit above analysis to the availability of a sufficient amount of data for image reconstruction, i.e., to $i > n/4$, because undersampling may otherwise dominate and complicate the motion classification. In other words, the repeated performing of the acquisition and analysis process may be started after a sufficient minimum amount of the MRI data of the set of MRI data has been acquired from the imaging zone of the magnetic resonance imaging system according to the pulse sequence commands.

It may also be required that the k-space trajectory is designed such that each time period contains MRI data from all parts of k-space to be sampled, i.e. even shares of central and outer k-space such that no time period contains (significantly) more MRI data from central and/or outer k-space than other time periods.

According to embodiments, the datasets have a common predefined size. Each dataset comprises magnetic resonance data from sampling points distributed over k-space with a higher sampling rate at the center of k-space relative to an outer portion of the sampled k-space.

According to embodiments, the distribution of sampling points in k-space and the order in which the sampling points are measured, i.e. magnetic resonance data is acquired from the respective sampling points, is chosen such that the successively acquired datasets each comprise a subset of magnetic resonance data which enables a meaningful processing of the respective dataset. The dataset may comprise a sufficient number of magnetic resonance data in order to avoid (excessive) undersampling. On the other hand, the dataset may not comprise too much magnetic resonance data in order to be able to detect any occurrence of a motion artifact promptly, if possible even instantaneous in real-time.

The sampling of the MRI datasets according to the pulse sequence commands may be performed analogous to key-hole imaging with the lower spatial frequencies being sampled with a higher rate than the higher spatial frequencies. The higher spatial frequencies may e.g. mainly be sampled by a first acquired MRI dataset which e.g. may comprise more data than the succeeding MRI datasets. According to embodiments, the succeeding MRI datasets may be focused on sampling lower spatial frequencies.

According to embodiments, the datasets have random sizes. Each dataset comprises magnetic resonance data from sampling points distributed over k-space with a higher sampling rate at the center of k-space relative to an outer portion of the sampled k-space. According to embodiments, the random sizes may be limited to be selected within a range defined by a predefined minimum and a maximum size. The sampling according to the pulse sequence commands may e.g. be performed using the golden-angle radial sampling scheme. Using the golden angle profile order for radially sampling the k-space with a consecutive profile spacing of 111.24 . . . ° (golden angle), a nearly uniform profile distribution may be guaranteed for an arbitrary number of successively acquired profiles. Thus, even though the MRI datasets may have random sizes (within limits), i.e. the time periods used for acquiring the MRI datasets may differ, each resulting MRI dataset may comprise a suitable distribution of sampling points. The distribution may in particular be suitable for avoiding ghosting.

According to embodiments, the maximum number of datasets is limited depending on the number of sampling points according to the pulse sequence commands.

According to embodiments, the memory further stores a first learning algorithm for generating the first machine learning model. The execution of the machine executable instructions further causes the processor to control the magnetic resonance imaging system to receive first training sets. Each first training set comprises a magnetic resonance imaging dataset and an artifact level identifier identifying an artifact level assigned to the respective magnetic resonance imaging dataset. The first learning algorithm is executed on the received first training sets for generating the first machine learning model.

Embodiments may have the beneficial effect of enabling an effective generation and/or configuration of the first machine learning model.

According to embodiments, the providing of the training set comprises generating magnetic resonance imaging datasets for training purposes with motion artifacts. The generating of the magnetic resonance imaging datasets for training purposes comprises introducing varying numbers, degrees and/or types of artificially generated motion artifacts to magnetic resonance imaging datasets without motion artifacts.

Embodiments may have the beneficial effect of providing an implementation of an automated generation of training set comprising a large number of magnetic resonance imaging datasets for training purposes with varying levels of motion artifacts. Such magnetic resonance imaging datasets for training purposes may e.g. be used for data augmentation purposes. Training of the deep learning network may thus be realized based on an automated generation of a large artificially generated datasets. Thereby, the need for large quantities of labeled input imaging datasets may be avoided.

For example, during a training stage, a labeled dataset may be used to train the deep learning network. During an application stage, the trained deep learning network is then applied to detect and classify motion artifacts in clinical magnetic resonance imaging datasets, like e.g. a clinical MRI image.

According to embodiments, trajectories of gross patient motion or physiological motion, in particular variants of translational or rotational motion trajectories, are selected from a group comprising e.g. discontinuous motion (e.g. "jumps", "jerks", "swallowing"), oscillating motion (e.g. "respiration"), and continuous motion (e.g. "bowel peristaltic motion", "head sinking into the cushion") simulated with varying motion amplitudes. Embodiments may have the beneficial effect that any type of motion can be prospectively simulated without having actual examples of MR data available that are actually corrupted by this motion type.

According to embodiments, the generation of magnetic resonance imaging datasets for training purposes with motion artifacts may comprise introducing a phase shift in k-space to one or more sections of magnetic resonance data of one or more of the motion-artifact-free magnetic resonance imaging datasets or direct translations of (sub-)portions of the image in image space. If processed in k-space, subsequently, the magnetic resonance imaging data including the motion simulation (e.g. phase shift) can be either directly stored as k-space training data or may additionally be transformed back from k-space to image space. For motion simulation in image space, again, image space and/or transformed k-space data can be stored for training purposes. Embodiments may have the beneficial effect that a large number of training sets (k-space or image space data) is efficiently provided based on artificially generated motion artifacts. This extensive simulated magnetic resonance data is advantageously used to train the deep learning network.

Since extensive training sets with labeled training images are often not available from the relevant application areas (e.g. hospitals), a method is described in the following that facilitates an artificial creation of a suitable training set (as described above) in combination with an automatic generation of the corresponding labels. Thus, a quantitative label for the level of motion artifacts contained in a current training set is provided. Starting from the Fourier shift theorem, a displacement T of the object in image space corresponds to a linear phase shift φ in k-space, $$S_m(\vec{k}) = S_s(\vec{k}) e^{i\varphi} = S_s(\vec{k}) e^{i2\pi \vec{k} \cdot \vec{T}},$$

where $S_m$ and $S_s$ are the images with and without displacement, respectively.

Any translational motion may thus be described by a parametrization of the vector $\vec{T}$. As an example, a shift of the object in y-direction may be simulated by introducing the following phase shift to the original data:

$$\varphi = 2\pi \cdot \vec{k} \cdot \vec{T} = 2\pi \cdot \delta k \cdot j \cdot n_s \cdot \Delta y = 2\pi \cdot j \cdot \frac{n_s}{N},$$

where $\delta k = 1/(N \cdot \Delta y)$ is an increment between adjacent phase encoding (PE) lines, j is a PE line index, $n_s$ is a displacement in numbers of pixels, and $\Delta y$ is a voxel size in PE direction. If the phase shift according to the equation above is applied to all PE lines, the entire object will be displaced in image space without any motion artifact. On the other hand, an abrupt patient motion during the scan may for example be simulated by applying the phase shift according to the equation above only to a subset of all k-space lines. In this case, it is assumed that the motion is happening as a point event m at some stage of the image acquisition. In case of a sequential k-space ordering, all lines with $j > j_m$ may have to be adjusted, where $j_m$ defines the PE line where the motion event m occurred. In case of other k-space ordering schemes, like e.g. center-out, interleaved, etc., the selection of PE lines where the phase shift is applied, has to be modified accordingly.

This approach for the simulation of magnetic resonance image motion artifacts involves the selection of several parameters that define the specific appearance of the artifacts: $n_s$, $j_m$, α, as well as the properties of the k-space ordering scheme. The described approach therefore allows for a fast generation of large artificial training sets by varying these parameters, which determine the type of motion artifact to be expected in the magnetic resonance images. Since the characteristics of the generated artifacts are known, generation of a list of motion-artifact-defining labels, i.e. motion artifact level identifiers, may be straightforward.

Once the deep learning network has been trained to allow for the detection of motion-related artifacts and/or determination of motion artifact level, it can may applied to actual clinical data for a detection of motion artifacts. According to embodiments, the output of the deep learning network may correspond to the labels that were employed during the training stage. In case of a pure detection of presence approach, the deep learning network may categorize input imaging datasets in terms of "artifact-free" and "artifact comprising". In case of a more complex classification approach, the deep learning network may categorize input imaging datasets in terms of classes of motion artifact level, such as e.g. "no artifact", "mild artifact", and "severe artifact". Alternatively, a regression algorithm instead of a classification algorithm may be employed yielding floating-point numbers that represent an estimate of the deep learning network regarding the individual motion artifact levels of the imaging datasets.

A rotational motion during a magnetic resonance imaging scan may be simulated in a way similar to the simulation of a translational motion. In this case, an appropriate transformation is applied to the object in image space. The transformation may be defined by the rotational angle α. Then, the k-space data of the original and the k-space data of the transformed images are combined. Again, the assumed k-space ordering scheme has to be taken into account for the selection of the PE lines for the combined images. An inverse Fourier transform applied to the combined images in k-space may yield an image with artificial motion artifacts due to rotational motion. Again, combined k-space data and/or transformed image space data may be stored for deep learning network training purposes.

According to embodiments, the magnetic resonance imaging datasets for training purposes are each assigned with a quantitative label describing the level of (simulated) motion artifacts which identifies the motion artifact level of the respective magnetic resonance imaging training data which is obtained as result of motion artifact simulation. According to embodiments, the motion artifact levels are determined depending on the values of the parameters used for generating the artificial motion artifacts.

According to embodiments, the determination of the motion artifact level of a magnetic resonance imaging training set may comprise comparing the magnetic resonance imaging datasets for training purposes with the motion-artifact-free magnetic resonance imaging datasets used for generating the respective magnetic resonance imaging datasets for training purposes. The motion artifact level may be determined depending on the degree of similarity between the imaging datasets compared. For example, the structural similarity (SSIM) index used for measuring the similarity between the two imaging datasets. The structural similarity (S SIM) index may provide an efficient automatic method for predicting the perceived quality of digital imaging datasets and thus to determine differences of the perceived quality between different imaging datasets. Embodiments may have the beneficial effect that a fully automated approach for providing a large number of magnetic resonance imaging datasets for training purposes labeled with motion artifact levels is provided.

According to embodiments, the magnetic resonance imaging datasets without motion artifacts are provided using a plurality of sets of magnetic resonance data without motion artifacts and from each set of magnetic resonance data a plurality of copies of magnetic resonance imaging datasets without motion artifacts are generated, each copy comprising a differently weighted magnetic resonance contrast. Embodiments may have the beneficial effect that an efficient approach for providing a large number of magnetic resonance imaging datasets for training purposes for training the deep learning network, e.g. in form of a fully convolutional network, as a filter for reducing the amount motion artifacts comprised by a magnetic resonance imaging dataset may be implemented.

Thus, the generation of synthetic imaging datasets based on quantitative magnetic resonance techniques may be employed to create magnetic resonance imaging datasets with additional contrasts. This approach may be used to extend the training to different magnetic resonance contrasts and to increase the size of the training set. To extend the proposed filtering mechanism to other magnetic resonance contrasts and to avoid limitation to a specific imaging protocol, the generation of synthetic magnetic resonance imaging datasets may contain contrast variations. Based on scans with quantitative measurements, e.g. for one or more of the following group: T1, T2, M0 (proton density), the appearance of anatomy with different protocol settings may be emulated.

According to embodiments, each of the magnetic resonance imaging dataset for training purposes is assigned with a motion artifact indicator. The motion artifact indicators indicate for each of the magnetic resonance imaging datasets for training purposes whether the respective magnetic resonance imaging datasets for training purposes comprises a motion artifact. The training comprises training the deep learning network for detecting the presence of motion artifacts magnetic resonance imaging datasets. The magnetic resonance imaging datasets for training purposes are applied as input to the deep learning network. For each of the magnetic resonance imaging datasets for training purposes it is determined whether motion artifacts are present in the respective magnetic resonance imaging datasets for training purposes using the trained deep learning network. A motion artifact indicator whether motion artifacts are present in the magnetic resonance imaging datasets for training purposes are provided as output from the deep learning network. The output of the deep learning network is compared with the motion artifact indicators assigned to the input to the deep learning network. Network parameters of the deep learning network are adapted in order to reduce differences between the output of the deep learning network and the motion artifact indicators assigned to the input to the deep learning network. Embodiments may have the beneficial effect that an effective and efficient way of training a deep learning network for detecting the presence of motion artifacts in magnetic resonance imaging datasets is provided.

According to embodiments, each of the magnetic resonance imaging datasets for training purposes is assigned with a motion artifact level identifier. The training comprises training the deep learning network for determining motion artifact levels of magnetic resonance imaging datasets. The magnetic resonance imaging datasets for training purposes are applied as input to the deep learning network. For each of the magnetic resonance imaging datasets for training purposes a motion artifact level of the respective magnetic resonance imaging datasets for training purposes is determined using the trained deep learning network. The motion artifact levels of the magnetic resonance imaging datasets for training purposes are provided as output from the deep learning network. The output of the deep learning network is compared with the motion artifact levels identified by the motion artifact level identifiers assigned to the input to the deep learning network. Network parameters of the deep learning network are adapted in order to reduce differences between the output of the deep learning network and the motion artifact levels identified by the motion artifact level identifiers assigned to the input to the deep learning network. Embodiments may have the beneficial effect that an effective and efficient way of training a deep learning network for determining the motion artifact level of magnetic resonance imaging datasets is provided.

According to embodiments, the execution of the machine executable instructions further causes the processor to control the magnetic resonance imaging system as follows: If a prediction received in a current repetition is increased relative to a prediction received in the last repetition preceding the current repetition, it is checked, whether omitting the current repetition results in a prediction received in the first repetition following the current repetition which is also increased relative to the prediction of the last repetition preceding the current repetition. If the omission results in no increase, the repeated performing of the acquisition and analysis process is continued with the current repetition omitted. Else continuing the repeated performing without omitting the current repetition.

Embodiments may have the beneficial effect of determining whether a motion artifact is limited to a single MRI dataset. If this is the case, the respective motion artifact may be removed by omitting the respective motion-artifact-corrupted dataset. According to embodiments, the omission of the respective MRI dataset may be possible without reducing the final image resolution to much. In this case, the respective MRI dataset may just be omitted. In case the respective MRI dataset is required for an accurate image reconstruction, the respective MRI dataset may either be re-scanned without requiring a re-scan of all the datasets or the respective MRI dataset may be replaced by a motion-artifact-corrected MRI dataset. The motion-artifact-corrected MRI dataset may be generated by providing the respective MRI dataset to the second input of a second machine learning model configured for motion artifact correction.

According to embodiments, the memory further stores a second machine learning model comprising a second deep learning network. The second machine learning model comprises a second input and a second output. An execution of the machine executable instructions further causes the processor to control the magnetic resonance imaging system as follows: If a prediction of the artifact level received in response to providing a dataset to the first input of the first machine learning model exceeds a second predefined threshold, the respective dataset is provided to the second input of the second machine learning model. A motion-artifact-corrected dataset is provided as a replacement for the respective dataset using a response received from the second output of the second machine learning model. The acquisition and analysis process is continued with the motion-artifact-corrected dataset.

Embodiments may have the beneficial effect of enabling in addition to the quality assessment by the first machine learning model an image quality optimization by the second machine learning model already during data acquisition. Thus, when the acquisition of all the subsets of the set of MRI data to be acquired according to the pulse sequence commands is finished, the respective set of MRI data may already have been optimized in order to minimize the effect of motion artifacts on the respective MRI data.

The second machine learning model is trained, i.e. configured, for filtering motion artifacts comprised by MRI datasets received via the second input. Depending on the training, i.e. configuration, of the second machine learning model, a filtering of the respective motion artifacts may for example result in a version of the received MRI datasets without the respective motion artifacts, i.e. a motion-artifact-corrected MRI dataset. Alternatively, the second machine learning model may be trained to return a motion-artifact-only MRI dataset comprising only the respective motion artifacts. A motion-artifact-corrected MRI dataset refers to a magnetic resonance imaging dataset in which motion artifacts have been minimized. In case the second machine learning model returns a version of the received MRI datasets without the respective motion artifacts via the second output, the respective version may be used for the replacing. Alternatively, in case a motion-artifact-only MRI dataset is returned via the second output, the respective motion-artifact-only MRI dataset may be subtracted from the MRI datasets provided to the second input, thus generating the motion-artifact-corrected dataset which is used for the replacement.

It may be easier for a deep learning network to be trained to identify and isolate data structures in MRI datasets which are due to motion artifacts and return the same as a motion-artifact-only MRI dataset than to identify all the data structures in MRI datasets which are not due to a motion artifact and to return the same as motion-artifact-corrected magnetic resonance imaging datasets. Embodiments may thus have the beneficial effect of enabling a more precise motion artifact correction based on a more precise identification of motion artifacts. According to embodiments, the motion-artifact-only magnetic resonance image may be displayed and/or stored in addition to the acquired set of corrected MRI data in order to provide additional insight in the motion artifacts occurred during data acquisition. For example, the positions of the corrected motion artifacts may be provided. Furthermore, displaying the motion-artifact-only magnetic resonance image may provide into which part of the original MRI data has been corrected and/or removed in order to provide the motion-artifact-corrected MRI data.

According to embodiments, the deep learning network of the second machine learning model is a fully convolutional neural network. The fully convolutional neural network may comprise a symmetric structure. It may e.g. comprise deconvoluting layers and/or un-pooling layers. Embodiments may have the beneficial effect that fully convolutional neural network may provide an effective filter for correction of motion artifacts.

Unlike deep convolutional neural networks for classification, a fully convolutional neural network, where deconvoluting and un-pooling layers replacing the fully connected layers used in deep convolutional neural networks for classification, may allow for an efficient generation of predictions at pixel level. A fully convolutional neural network may thus be applied as a motion artifact filter for reducing the motion artifact level of the MRI datasets.

According to embodiments, the proposed filtering concept may be adapted to alternative data sources and/or additional input. Embodiments may e.g. make use of complex k-space data which is obtained during the acquisition of magnetic resonance data during a magnetic resonance scan. Embodiments may further use complex data of individual receive coil elements of a magnetic resonance imaging system to exploit inherent redundancy in multi-channel data.

A fully convolutional neural network may be provided with the acquired MRI datasets, while the data acquisition is still ongoing, using the complex raw data. Alternatively, the fully convolutional neural network may be employed to reduce motion artifacts in magnetic resonance images reconstructed or partially reconstructed from the respective raw data. In other words, the MRI data comprised by the MRI dataset provided to the second input of the second machine learning input may be provided in k-space or image space representation.

According to embodiments, the memory further stores a second learning algorithm for generating the second machine learning model. The execution of the machine executable instructions further causes the processor to control the magnetic resonance imaging system to receive second training sets. Each second training set comprising a magnetic resonance imaging dataset and a motion-artifact-only magnetic resonance imaging dataset assigned to the respective magnetic resonance imaging dataset. The second learning algorithm is executed on the second received training sets for generating the second machine learning model.

Embodiments may have the beneficial effect of enabling an effective training, i.e. configuration, of the second machine learning model. After successful training, the second machine learning model comprising the deep learning network may allow for correction of artifacts in MRI data during acquisition without relying on knowledge of the precise motion trajectory. For example, a fully convolutional neural network may be employed for filtering motion artifacts relying on a two-phase procedure. In a first phase, a large number of artificial second training sets may be generated using motion-artifact-free MRI reference datasets. In a second phase, the fully convolutional neural network may be trained for motion artifact correction using the generated artificial second training sets, while the resulting second machine learning model with the trained fully convolutional neural network may be applied as a filter to actual motion-artifact-corrupted MRI datasets in order to generate MRI datasets with a substantially reduced motion artifact level already during data acquisition.

According to embodiments, the training set further comprises for each of the magnetic resonance imaging datasets for training purposes a magnetic resonance imaging reference dataset assigned to the respective magnetic resonance imaging datasets for training purposes. The magnetic resonance imaging reference datasets is a motion-artifact-free version of the magnetic resonance imaging datasets for training purposes to which it is assigned. The training comprises training the deep learning network for filtering motion artifacts present in magnetic resonance imaging datasets. The magnetic resonance imaging datasets for training purposes are applied as input to the deep learning network. Motion artifacts of the magnetic resonance imaging datasets for training purposes are filtered using the trained deep learning network. For each of the magnetic resonance imaging datasets for training purposes motion-artifact-corrected magnetic resonance imaging datasets are provided using a result of the filtering. The motion-artifact-corrected magnetic resonance imaging datasets are compared with the magnetic resonance imaging reference datasets and network parameters of the deep learning network are adapted in order to reduce differences between motion-artifact-corrected magnetic resonance imaging datasets and the magnetic resonance imaging reference datasets. Embodiments may have the beneficial effect that an effective and efficient way of training a deep learning network for filtering motion artifacts present in magnetic resonance imaging datasets is provided.

Using a training set as described above comprising pairs of magnetic resonance imaging datasets for training purposes and assigned magnetic resonance imaging reference datasets and using a suitable objective function, like e.g. the difference between the output of the fully convolutional neural network and the magnetic resonance imaging reference datasets of the training pair without motion artifacts, weights of the fully convolutional neural network may be optimized using suitable techniques such as stochastic gradient descent.

According to embodiments, the result of the filtering comprises the motion-artifact-corrected magnetic resonance imaging datasets which are provided as output from the deep learning network. Embodiments may have the beneficial effect that an effective and efficient way of training a deep learning network for generating motion-artifact-corrected magnetic resonance imaging datasets is provided.

According to embodiments, the result of the filtering comprises motion-artifact-only magnetic resonance imaging datasets provided as output from the deep learning network and the providing of the motion-artifact-corrected magnetic resonance imaging datasets comprises subtracting the motion-artifact-only magnetic resonance imaging datasets from the magnetic resonance imaging datasets for training purposes. Embodiments may have the beneficial effect that an effective and efficient way of training a deep learning network for motion-artifact-only magnetic resonance imaging datasets is provided.

According to embodiments, the magnetic resonance imaging datasets for training purposes are applied in batches to the deep learning network. According to embodiments, the comparison between the output resulting from applying the batches and the intended output for which the deep learning network is trained, i.e. the correct motion artifact indicators, motion artifact levels, motion-artifact-corrected magnetic resonance imaging datasets, motion-artifact-only magnetic resonance imaging datasets etc., is perform statistically using statistics of the batch.

According to embodiments, the network parameters may be adapted using techniques like e.g. backpropagation. Backpropagation is used to calculate the error contribution of each neuron of the network after a batch of data, i.e. magnetic resonance imaging datasets for training purposes, is processed. This may be used by an enveloping optimization algorithm to adjust the weight of each neuron.

Thus, a tailored multi-resolution deep learning network, e.g. deep convolutional neural network or fully connected neural network, may be implemented for motion artifact detection, motion artifact level determination or retrospective motion artifact correction. In order to construct such a tailored multi-resolution deep learning network, a deep learning network may be trained using a large number of training sets with artificially created motion artifacts introduced e.g. onto in vivo, clinical brain scans. For example, for brain imaging the motion simulation may comprise translations and rotations of a patient's head at various time steps and with different intensity.

According to embodiments, the network parameters of the deep learning network are adapted using an iterative adjustment. The iterative adjustment comprises a plurality of cycles of iteration. Each cycle of iteration comprises determining differences between the resulting output of the deep learning network and the intended output for which the deep learning network is trained. According to embodiments, the iterative adjustment is terminated, if the number cycles of iteration reaches a predefined first threshold or if the differences between the resulting output of the deep learning network and the intended output reach a predefined second threshold. For determine the differences statistics over batches may be used. Additional, the performance on separate test or validation dataset can be monitored in order to avoid overfitting.

According to embodiments, pre-training strategies may be considered in order to avoid the need for large labeled magnetic resonance datasets for training purposes. Existing deep learning networks, which are not trained for processing motion artifact in magnetic resonance imaging datasets, may be used as generic feature extractors, while certain layers may be replaced and/or fine-tuned for the specific application, i.e. processing motion artifact in magnetic resonance imaging datasets.

According to embodiments, in addition to features that are extracted by the deep learning network, traditional features for motion artifact estimation, like e.g. motion artifact presence detection or artifact level determination, may be employed. For example, gradient based features may be used as additional input, e.g. for the fully connected layers in case of a deep convolutional network.

Furthermore, strategies for a re-training on the deep learning network may be taken into account. Based on a user feedback, e.g. a rating of the imaging datasets by a radiologic technologist or radiologist, a re-training of the deep learning network may be triggered in order to adapt the deep learning network to local guidelines and preferences as well as to train the deep learning network to detect additional types of artifacts.

In another aspect, the invention relates to a computer program product comprising machine executable instructions for execution by a processor controlling a magnetic resonance imaging system using pulse sequence commands and a first machine learning model comprising a first deep learning network. The pulse sequence commands are configured for controlling the magnetic resonance imaging system to acquire a set of magnetic resonance imaging data. The first machine learning model comprises a first input and a first output.

An execution of the machine executable instructions causes the processor to repeatedly perform an acquisition and analysis process comprising acquiring a dataset comprising a subset of the set of magnetic resonance imaging data from an imaging zone of the magnetic resonance imaging system according to the pulse sequence commands. The dataset is provided to the first input of the first machine learning model. In response of the providing of the dataset to the first input, a prediction of a motion artifact level of the acquired magnetic resonance imaging data is received from the first output of the first machine learning model. The motion artifact level characterizes a number and/or extent of motion artifacts present in the acquired magnetic resonance imaging data.

In another aspect, the invention relates to method of operating a magnetic resonance imaging system. The magnetic resonance imaging system comprises a memory storing machine executable instructions, pulse sequence commands and a first machine learning model comprising a first deep learning network. The pulse sequence commands are configured for controlling the magnetic resonance imaging system to acquire a set of magnetic resonance imaging data. The first machine learning model comprises a first input and a first output. The magnetic resonance imaging system comprises a processor for controlling the magnetic resonance imaging system.

The method comprises repeatedly perform an acquisition and analysis process comprising acquiring a dataset comprising a subset of the set of magnetic resonance imaging data from an imaging zone of the magnetic resonance imaging system according to the pulse sequence commands. The dataset is provided to the first input of the first machine learning model. In response of the providing of the dataset to the first input, a prediction of a motion artifact level of the acquired magnetic resonance imaging data is received from the first output of the first machine learning model. The motion artifact level characterizes a number and/or extent of motion artifacts present in the acquired magnetic resonance imaging data.

Embodiments may comprise an acquisition of MRI data, wherein the acquired MRI data is directly analyzed, while the acquisition is still ongoing. The data analysis is executed on subsets of the MRI data in the order of acquisition. As soon as the acquisition of an MRI subset is complete, the respective subset is provided to a first machine learning model. According to embodiments the respective subset is provided to the first machine learning model either individually or in combination with all the other subsets of the MRI data acquired so far. The first machine learning model is configured to provide a prediction of the motion artifact level of the MRI data provided to the first machine learning model, i.e. an individual subset or all the subsets acquired so far. Thus, the motion artifact level of the acquired MRI data may be monitored during data acquisition.

The aforementioned embodiments of the invention may enable to monitor the motion artifact level of MRI data which is acquired during the acquisition and thus detect the occurrence of motion artifacts at an early stage. Thus, there is no need to wait until the full data acquisition is completed before it may be checked whether and to which extent the acquired MRI data comprises motion artifacts. In addition, appropriate measures may thus be enabled at an early stage, like abortion of the data acquisition, starting a re-scan, instructing the patient and/or trying to correct the MRI data using post-processing.

In addition, a second machine learning model may be provided for a motion artifact correction based on post-processing. The machine learning model is configured to provide either a motion-artifact-corrected or a motion-artifact-only MRI dataset in response to receiving an MRI dataset. In case motion artifacts are detected by the first machine learning model, the MRI dataset(s) comprising these motion artifacts may be corrected using the second machine learning model. Either the received motion-artifact-corrected MRI dataset is used as a replacement for the motion-artifact-corrupted MRI dataset or the motion-artifact-only MRI dataset is subtracted from the motion-artifact-corrupted MRI dataset resulting in the desired motion-artifact-corrected MRI dataset.

In addition, embodiments enable to identify whether the occurrence of a motion artifact is limited to one or more consecutively acquired MRI datasets. In case the respective one or more MRI datasets cause an increase of the motion artifact level, while no such increase occurs, when omitting the respective one or more MRI datasets, then the motion artifact and its effects are restricted to the respective one or more consecutively acquired MRI datasets: The patient moves, but returns into the initial position before the movement. Consequently, the all the remaining MRI datasets are consistent and in particular the anatomical structures of interest to be pictured have remained at a constant position, while the respective MRI datasets have been acquired. Thus, only the one or more MRI datasets with the motion artifact may have to be re-acquired, but not all of the MRI datasets.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance Imaging (MRI) data, also referred to as Magnetic Resonance (MR) data, is defined herein as being the recorded measurements of radio frequency signals emitted by nuclear spins using the antenna of a magnetic resonance apparatus during a magnetic resonance imaging scan. Magnetic resonance imaging data is an example of medical image data. A Magnetic Resonance Imaging (MRI) image or MR image is defined herein as being the reconstructed two or three-dimensional visualization of anatomic data comprised by the magnetic resonance imaging data, i.e. MRI images are provided by MRI datasets comprising a representative selection MRI data. This visualization can be performed using a computer. Magnetic resonance imaging data may be provided using a representation of the respective data in k-space or image space. Using a Fourier transformation, the magnetic resonance imaging data may be transformed from k-space to image space or vice versa. In the following, a magnetic resonance imaging dataset may comprise MRI data in k-space or image space. In particular, magnetic resonance imaging datasets may comprise a selection of MRI data in image space representative of a two or three-dimensional anatomic structure.

The term 'machine learning' refers to a computer algorithm used to extract useful information from training datasets by building probabilistic models (referred to as machine learning models) in an automated way. The machine learning may be performed using one or more learning algorithms such as linear regression, k-nearest neighbor techniques, support vector machines or classification/regression trees etc. A 'model' may for example be an equation or set of rules that makes it possible to predict an unmeasured value (e.g. which tag corresponds to a given token) from other, known values and/or to predict or select an action to maximize a future reward.

A 'deep learning network' or 'deep learning network' as used herein encompasses a machine learning model in form of a network, like e.g. neural networks, with multiple hidden layers between an input and an output layer. Deep learning refers to a class of machine learning methods which use a cascade of multiple layers of nonlinear processing units for feature extraction and transformation. Each successive layer uses the output from the previous layer as input. Deep learning may be performed supervised and/or unsupervised. Furthermore, deep learning may use some form of gradient descent for training via backpropagation.

'Neural networks' as used herein encompasses are computing systems configured to learn, i.e. progressively improve their ability, to do tasks by considering examples, generally without task-specific programming. A neural network comprises a plurality of units referred to as neurons which are communicatively connected by connections for transmitting signals between connected neurons. The connections between neurons are referred to as synapses. Neurons receive a signal as input, change their internal state, i.e. the activation, according to the input. Depending on the input, the learned weights and bias an activation is generated as output (optionally using a dedicated activation function like ReLU) and sent via one or more synapses to one or more connected neurons. The network forms a directed and weighted graph, where the neurons are the nodes and the connection between the neurons are weighted directed edges. The weights and biases may be modified by a process called learning, which is governed by a learning rule. The learning rule is an algorithm which modifies the parameters of the neural network, in order for a given input to the network to produce a favored output. This learning process may amount to modifying the weights and biases of the network.

The neurons are organized in layers. Different layers may perform different types of transformations on their inputs. Signals applied to a neuronal network travel from a first layer, i.e. the input layer, to the last layer, i.e. output layer, traversing hidden layers arranged between input and output layer.

'Network parameters' as used herein encompass weights and biases of the neurons which may be varied as learning proceeds and which may increase or decrease the strength of signals that are sends downstream by the neurons via the synapses.

A 'deep convolutional neural network' as used herein encompasses a deep, feed-forward neural network comprising a plurality of convolutional layers with one or more fully connected layers on top. Furthermore, a deep convolutional neural network' may comprises pooling layers, e.g. max-pooling layers or average-pooling layer. Convolutional layers apply a convolution operation to the input, passing the result to the next layer. Furthermore, convolutional layers share weights, i.e. all weights of a convolutional layer are identical. Pooling layers merge the outputs of neuron clusters at one layer into an input to a single neuron in the next layer. For example, max pooling layers use for each neuron cluster a maximum value of the outputs as input for the next layer. Another example are average pooling layers, which use an average value of the outputs as input for the next layer. Fully connected layers connect every neuron in one layer to every neuron in another layer. A deep convolutional neural network may comprise further layer types, like e.g. rectified-linear unit layers (ReLU layers), batch normalization layers (BN-layers), dropout layer etc.

A 'fully convolutional neural network' as used herein encompasses a convolutional neural network comprising no fully connected layers. In contrast to a convolutional network, a fully convolutional neural network may exhibit a symmetric structure, where the fully connected layers are replaced by un-pooling and/or de-convolutional layers including skip connections between high resolution layers. While a deep convolutional neural network computes a general nonlinear function, a fully convolutional neural network with only layers of the aforementioned form computes a nonlinear filter. Fully convolutional networks may comprise in addition to convolutional layers and pooling layers un-pooling layers and/or de-convolutional layers and/or further layer types, like e.g. rectified-linear unit layers (ReLU layers), batch normalization layers (BN-layers), dropout layer etc.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
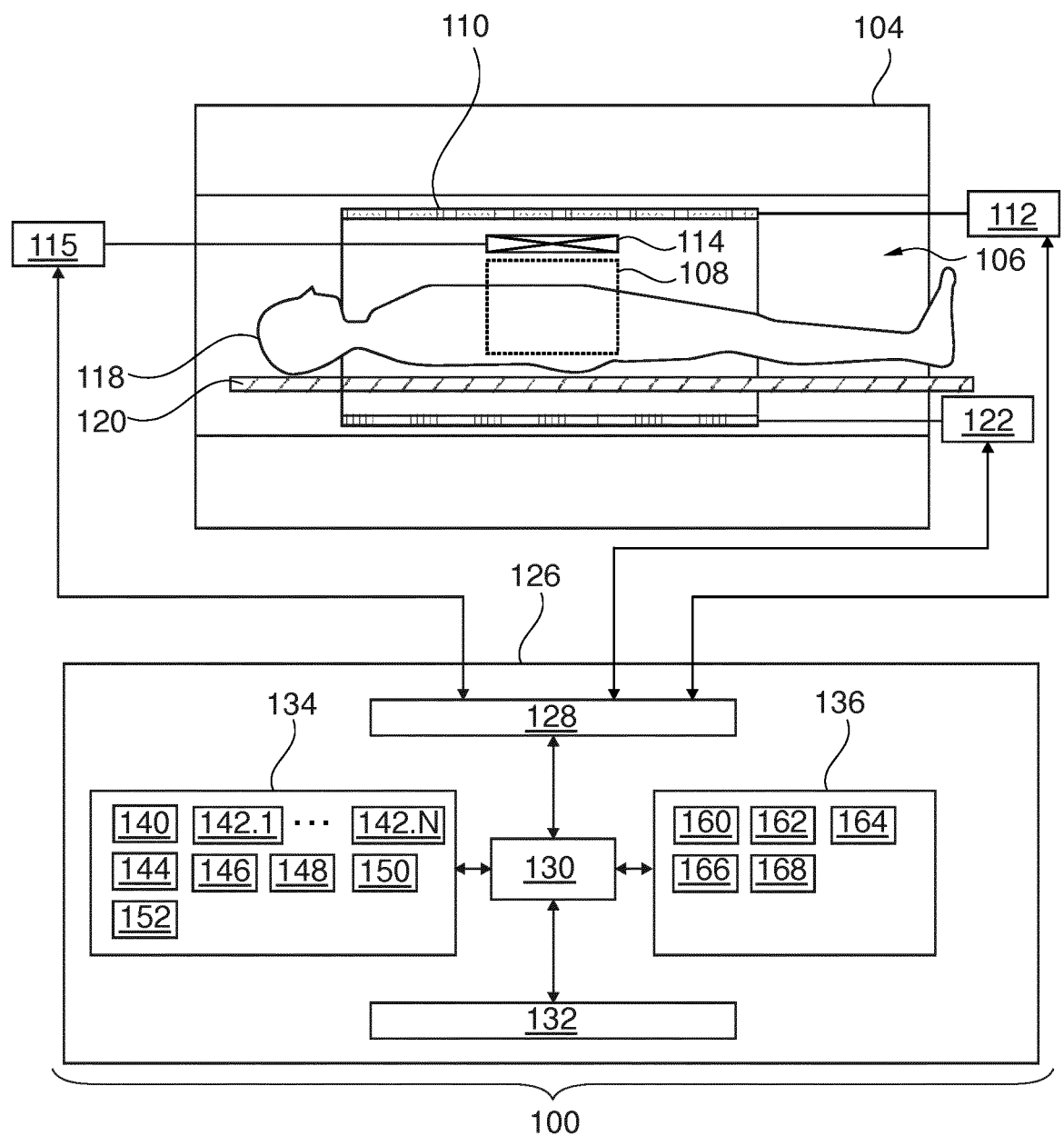
FIG. 1 illustrates a first example of a magnetic resonance imaging system.

FIG. 1 shows an example of a magnetic resonance imaging system 100 with a magnet 104. The main magnet 104 is a superconducting cylindrical type magnet 104 with a bore 106 through it. The use of different types of magnets is also possible. For instance, it is also possible to use both a split cylindrical magnet and a so called open magnet. A split cylindrical magnet is similar to a standard cylindrical magnet, except that the cryostat has been split into two sections to allow access to the axial plane through the iso-center of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is an imaging zone 108 where the magnetic field is strong and uniform enough to perform magnetic resonance imaging.

Within the bore 106 of the magnet there is also a set of magnetic field gradient coils 110 forming a magnetic field gradient system which is used for acquisition of magnetic resonance data to spatially encode magnetic spins within the imaging zone 108 of the magnet 104. The magnetic field gradient coils 110 connected to a magnetic field gradient coil power supply 112. The magnetic field gradient coils 110 are intended to be representative. Typically, magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114, also referred to as radio-frequency antenna system, for manipulating the orientations of magnetic spins within the imaging zone 108 and for receiving radio transmissions from spins also within the imaging zone 108. The radio-frequency coil 114 may contain multiple coil elements. The radio-frequency coil 114 is connected to a radio frequency transceiver 115. The radio-frequency coil 114 and radio frequency transceiver 115 may be replaced by separate transmit and receive coils and a separate transmitter and receiver. It is understood that the radio-frequency coil 114 and the radio frequency transceiver 115 are representative. The radio-frequency coil 114 is intended to also represent a dedicated transmit antenna and a dedicated receive antenna. Likewise, the transceiver 115 may also represent a separate transmitter and receivers. The radio-frequency coil 114 may also have multiple receive/transmit elements and the radio frequency transceiver 115 may have multiple receive/transmit channels.

The subject support 120 is attached to an optional actuator 122 that is able to move the subject support and the subject 118 through the imaging zone 108. In this way, a larger portion of the subject 118 or the entire subject 118 can be imaged. The transceiver 115, the magnetic field gradient coil power supply 112 and the actuator 122 are shown as being connected to a hardware interface 128 of computer 126.

The computer 126 is further shown as containing a processor 130 which is operable for executing machine-readable instructions. The computer 126 is further shown as comprising a user interface 132, computer storage 134 and computer memory 136 which are all accessible and connected to the processor 130.

The computer storage 134 may contain one or more pulse sequences 140. The pulse sequences 140 are either instructions or data which can be converted into instructions which enable the processor 130 to acquire magnetic resonance data using the magnetic resonance imaging system 100.

The computer storage 134 is further shown as containing a plurality of magnetic resonance imaging datasets 142.1, . . . , 142.N acquired by the radio-frequency coil 114. Each of the magnetic resonance imaging datasets 142.1, . . . , 142.N may comprise a subset a set of magnetic resonance data acquired in a 3D data acquisition mode of the MRI system 100 according to the pulse sequences 140. The computer storage 134 may further comprise a combined set of magnetic resonance imaging data 144 comprising a combination of all the magnetic resonance imaging datasets 142.1, . . . , 142.N acquired so far. Each time, the acquisition of a further magnetic resonance imaging datasets 142.1, . . . , 142.N is finished, the respective further magnetic resonance imaging datasets 142.1, . . . , 142.N is added to the combined set of magnetic resonance imaging data 144. The combined set of magnetic resonance imaging data may either comprise k-space data or a magnetic resonance image reconstructed using the combination of the magnetic resonance imaging datasets 142.1, . . . , 142.N acquired so far.

Preferably, the k-space is divided into n data segments along the time axis with n chosen such that each segment contains a relevant chunk of data, e.g. 5<n<10. As soon as a time segment $P_i$ is fully acquired, a 3D image $Im_i$ is reconstructed using all data segments $P_k$ with k≤i, i.e. all available data at this time point. This typically results in an image with less than the final resolution. This image is subjected to the motion classifier performed by the CNN which may result in a motion level $L_i=C(Im_i)$. If $L_i>L_i-1$, i.e. if the artefact level rises on inclusion of the latest data segment, then it is likely that the patient has moved during the respective time period Thus, for an image based approach, the input size for the network can be fixed as an image could be re-construct with an appropriate (fixed) resolution.

When instead k-space data is used, the network could be provided with a e.g. sparse matrix of a fixed size using the input from 142.1-142.N.

The computer storage 134 is further shown as containing a first machine learning model 146 configured for predicting motion artifact levels. The first machine learning model may comprise a trained deep learning network, e.g. in form of a trained deep convolutional neural network.

In addition, the computer storage 134 may comprise results 148 resulting from applying the combined set of magnetic resonance imaging data 144 to the first machine learning model 146 each time a further magnetic resonance imaging dataset 142.1, . . . , 142.N has been acquired and added to the combined set of magnetic resonance imaging data 144. According to embodiments, the first magnetic resonance imaging dataset 142.1 may be larger than the remaining magnetic resonance imaging datasets 142.2, . . . , 142.N. Thus, it may be ensured that the combined set of magnetic resonance imaging data 144 comprises at least a predefined minimum magnetic resonance data, when being provided to the first machine learning model 146. In particular, in case the combined set of magnetic resonance imaging data 144 comprises a reconstructed magnetic resonance image, this may avoid an undersampling. For example, the first magnetic resonance imaging dataset 142.1 may comprise a quarter of the set of magnetic resonance data to be acquired according to the pulse sequences 140. The remaining magnetic resonance imaging datasets 142.2, . . . , 142.N may be of a common predefined size or of different random sizes within a range defined by a predefined minimum and a predefined maximum size.

The first machine learning model 146 may be fully configured, i.e. trained, externally and provided to the computer storage 134 in trained form. Alternatively, the first machine learning model 146 may be preconfigured, i.e. pretrained, to a certain extent externally and further trained locally by the computer 126 after being stored in the computer storage 134. Alternatively, the first machine learning model 146 may be locally configured, i.e. trained, from scratch by the computer 126.

In case the first machine learning model is at least partially trained by the computer 126, the computer storage 134 may further contain a first learning algorithm 150 for generating and/or configuring the first machine learning model 146. Furthermore, the computer storage 134 may further contain a plurality of first training sets 152 to be used by the first learning algorithm 150 in order to generate and/or configurate the first machine learning model 146. Each first training set 152 may comprise a magnetic resonance imaging dataset and an artifact level identifier identifying an artifact level assigned to the respective magnetic resonance imaging dataset. The first machine learning model 146 may be generated and/or configured by executing the first learning algorithm 150 on the first training sets 152.

The computer memory 136 is shown as comprising a control module 160. The control module 160 contains computer executable code or instructions which enable the processor 130 to control the operation and function of the magnetic resonance imaging system. For instance, the control module 160 may work in conjunction with the pulse sequences 140 to acquire the various magnetic resonance imaging datasets 142.1, . . . , 142.N and combine the acquired magnetic resonance imaging datasets 142.1, . . . , 142.N generating the combined set of magnetic resonance imaging data 144. In case the combined set of magnetic resonance imaging data 144 comprises a magnetic resonance image reconstructed from the various magnetic resonance imaging datasets 142.1, . . . , 142.N, the computer memory 136 may further contain an imaging reconstruction module 162 which contains computer executable code or instructions which enable the processor 130 to control the operation and function of the magnetic resonance imaging system to reconstruct magnetic resonance images.

The computer memory 136 may further contain an analysis module 164. The analysis module 164 contains computer executable code or instructions which enable the processor 130 to apply the combined set of magnetic resonance imaging data 144 to the first machine learning model 146 and to generate the results 148. The results 148 may for example comprise one or more predictions of motion artifact levels assigned to the combined set of magnetic resonance imaging data 144.

Furthermore, the computer memory 136 may comprise a training module 166 containing computer executable code or instructions which enable the processor 130 to generate/configure the first machine learning model 146 using the first learning algorithm 150 in combination with the first training sets 152.

Finally, computer memory 136 may comprise a motion artifact simulation module 168 containing computer executable code or instructions. The computer executable code or instructions of the motion artifact simulation module 168 enable the processor 130 to generate magnetic resonance imaging datasets with artificially calculated motion artifacts for the first training sets 152 by simulating and introducing varying numbers, extents and/or types of artificially generated motion artifacts to one or more motion-artifact-free magnetic resonance images.

Figure 2:
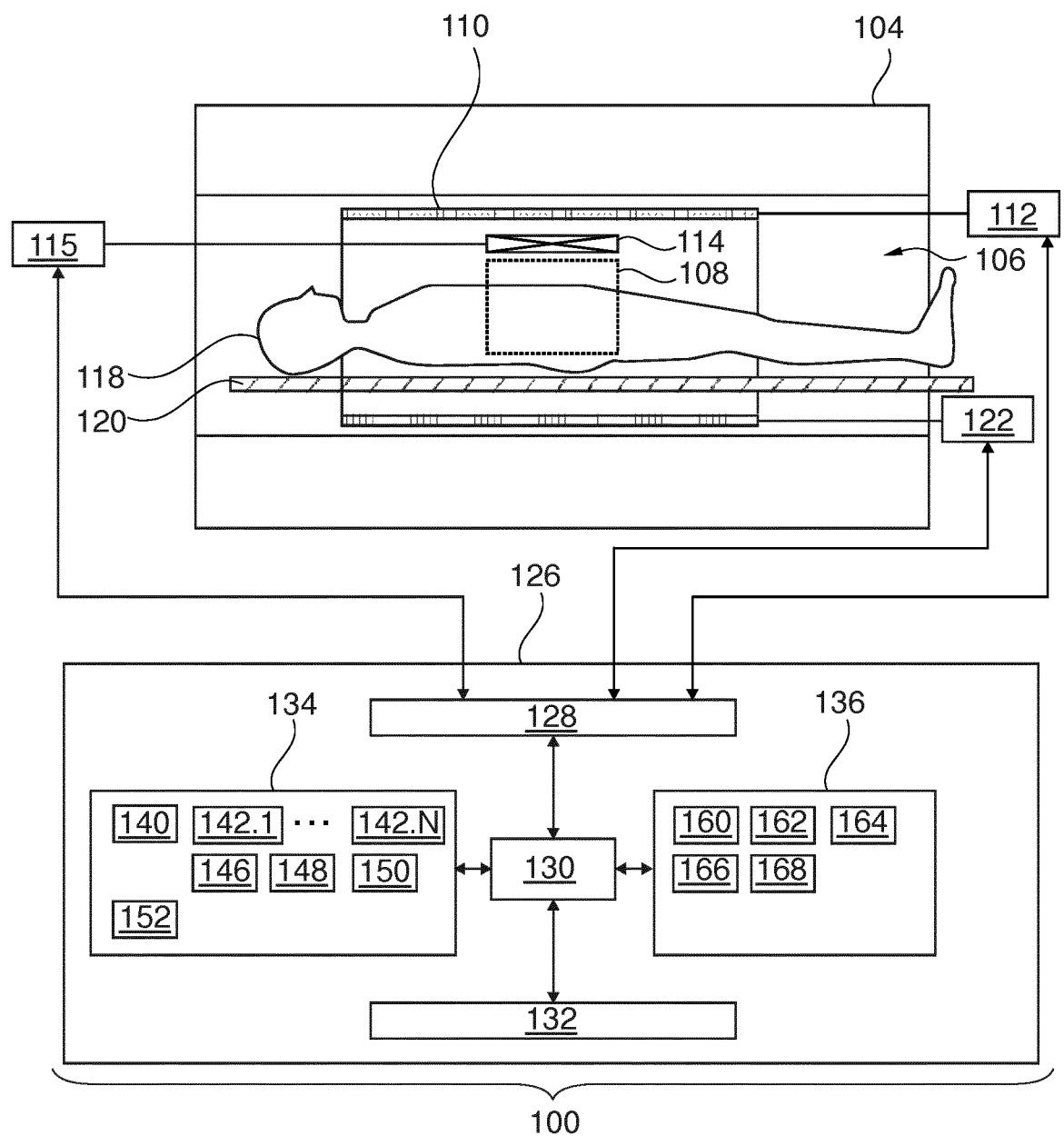
FIG. 2 illustrates a second example of a magnetic resonance imaging system.

FIG. 2 shows an example of an alternative embodiment of the magnetic resonance imaging system 100 of FIG. 1. In case of the alternative embodiment, each of the magnetic resonance imaging datasets 142.1, . . . , 142.N may comprise a subset of a set of magnetic resonance data in form of a 2D slice through the imaging zone 108 acquired in a multi-2D data acquisition mode of the MRI system 100 according to the pulse sequences 140. The result is a stack of 2D slices, wherein each of them may be provided by one of the magnetic resonance imaging datasets 142.1, . . . , 142.N. The magnetic resonance imaging datasets 142.1, . . . , 142.N may comprise the acquired MRI data either in form of k-space data of a 2D slice or a reconstructed magnetic resonance image of the respective slice. In contrast to the embodiment of FIG. 1, the magnetic resonance imaging datasets 142.1, . . . , 142.N are each provided to the first machine learning model 146 without being combined. Thus, the first machine learning model 146 may return predictions of the motion artifact levels of the individual 2D slices. The results 148 may comprise these predictions. In addition, the results 148 comprise a prediction of an averaged motion artifact level of the stack of 2D slices calculated from the individual predictions received from the first machine learning model 146. In order to evaluate a motion artifact level characterizing the full stack of 2D slices, e.g. either the averaged motion artifact level or the largest one of the individual motion artifact level of the 2D slices may be used and compared with a predefined threshold. Furthermore, the control module 160 may in contrast to the embodiment of FIG. 1 not be configured to combine the magnetic resonance imaging datasets 142.1, . . . , 142.N.

In case the magnetic resonance imaging datasets 142.1, . . . , 142.N comprise reconstructed magnetic resonance images of the 2D slices, the imaging reconstruction module 162 of computer memory 136 may contain computer executable code or instructions which enable the processor 130 to control the operation and function of the magnetic resonance imaging system to reconstruct the respective magnetic resonance images of the individual magnetic resonance imaging datasets 142.1, . . . , 142.N using the underlying MRI raw data acquired by the by the radiofrequency coil 114.

Figure 3:
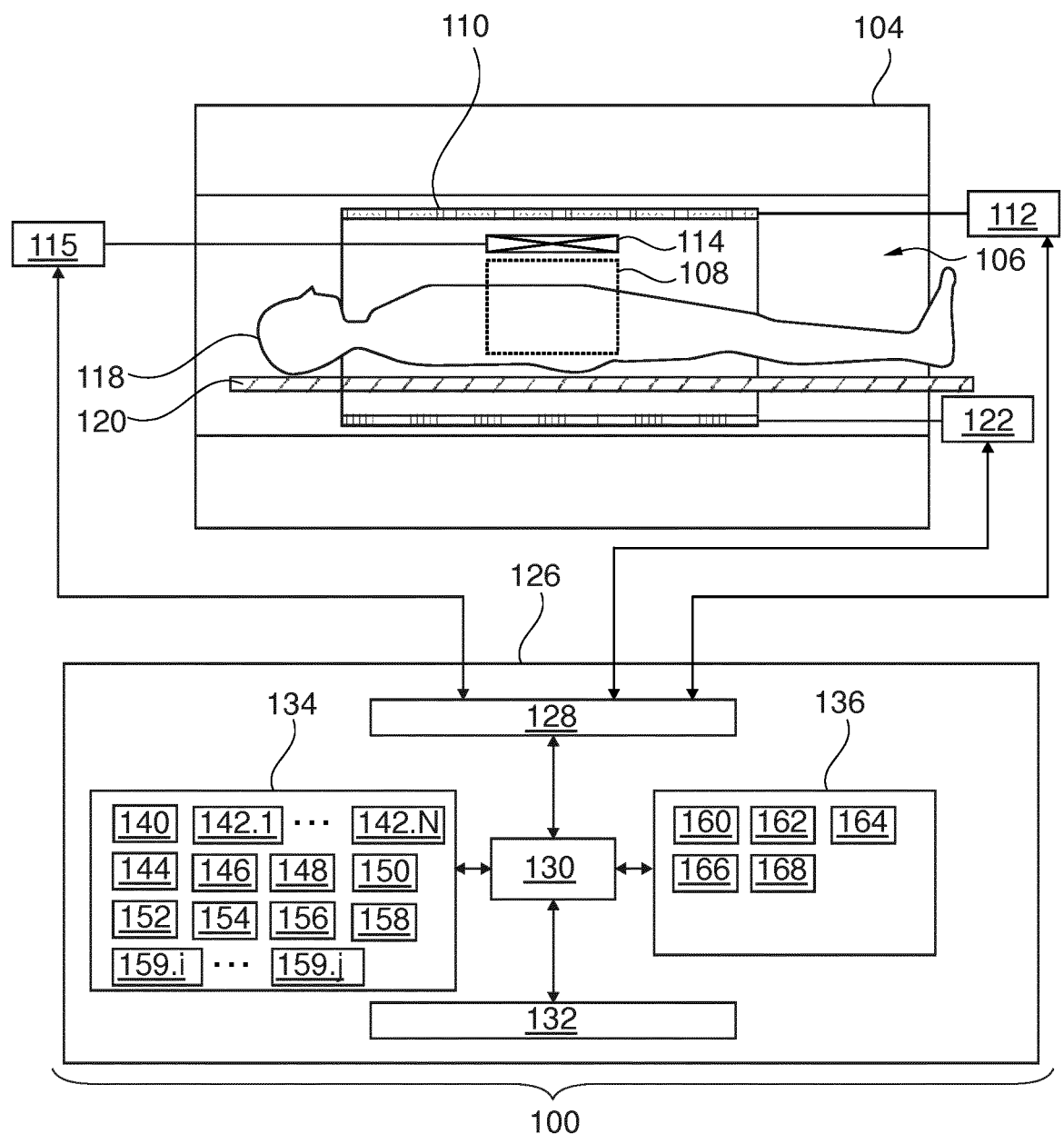
FIG. 3 illustrates a third example of a magnetic resonance imaging system.

FIG. 3 shows an example of a further alternative embodiment of the magnetic resonance imaging system 100 of FIG. 1. In addition to the data objects shown in FIG. 1, the computer storage 134 of FIG. 3 further contains a second machine learning model 154 configured for filtering and/or correcting motion artifacts comprised by the magnetic resonance imaging datasets 142.1, . . . , 142.N. According to embodiments, the magnetic resonance imaging datasets 142.1, . . . , 142.N may each be provided to the second machine learning model 154 on default resulting in motion-artifact-corrected magnetic resonance imaging datasets 159.i, . . . , 159.j, with i= and j=N.

Further, the resulting motion-artifact-corrected magnetic resonance imaging datasets 159.i, . . . , 159.j may be combined in order to generate the combined set of magnetic resonance imaging data 144. In case the second machine learning model 154 is configured to return upon receiving of a magnetic resonance imaging dataset 142.1, . . . , 142.N via the second input an artifact corrected magnetic resonance imaging dataset 159.i, . . . , 159.j via the second output, the respective artifact corrected magnetic resonance imaging datasets 159.i, . . . , 159.j may be directly used for generating the combined set of magnetic resonance imaging data 144. In case the second machine learning model 154 is configured to return upon receiving of a magnetic resonance imaging dataset 142.1, . . . , 142.N via the second input an artifact only magnetic resonance imaging dataset 159.i, . . . , 159.j via the second output, the returned artifact only magnetic resonance imaging dataset 159.i, . . . , 159.j may be subtracted from the magnetic resonance imaging dataset 142.1, . . . , 142.N provided to the second machine learning model 154 in order to provide an artifact corrected magnetic resonance imaging dataset 159.i, . . . , 159.j which may be used for generating the combined set of magnetic resonance imaging data 144.

According to alternative embodiments, a magnetic resonance imaging dataset 142.1, . . . , 142.N is provided to the second machine learning model 154 resulting in a motion-artifact-corrected magnetic resonance imaging dataset 159.i, . . . , 159.j, in case the respective magnetic resonance imaging dataset 142.1, . . . , 142.N is determined by the first machine learning model 146 to comprise one or more motion artifacts, i.e. to contribute to an increase of the predicted motion artifact level. A magnetic resonance imaging dataset 142.i may in particular be provided to the second machine learning model 154, in case this results in a singular increase of the predicted motion artifact level, i.e. in case neither the preceding magnetic resonance imaging dataset 142.i−1 nor the succeeding magnetic resonance imaging dataset 142.i−1 results in an increase of the predicted motion artifact level.

In case one of magnetic resonance imaging datasets 142.1, . . . , 142.N is motion artifact free, the corresponding artifact corrected magnetic resonance imaging datasets 159.i, . . . , 159.j may be identical. In case one of magnetic resonance imaging datasets 142.1, . . . , 142.N comprises a motion artifact, the corresponding corrected magnetic resonance imaging datasets 159.i, . . . , 159.j may comprise all the data of the respective magnetic resonance imaging datasets 142.1, . . . , 142.N except for the data influenced by the motion of the subject.

The second machine learning model 154 may be fully configured, i.e. trained, externally and provided to the computer storage 134 in trained form. Alternatively, the second machine learning model 154 may be preconfigured, i.e. pretrained, to a certain extent externally and further trained locally by the computer 126 after being stored in the computer storage 134. Alternatively, the second machine learning model 154 may be locally configured, i.e. trained, from scratch by the computer 126.

In case the second machine learning model is at least partially trained by the computer 126, the computer storage 134 may further contain a second learning algorithm 156 for generating and/or configuring the second machine learning model 154. Furthermore, the computer storage 134 may further contain a plurality of second training sets 158 to be used by the second learning algorithm 156 in order to generate and/or configurate the second machine learning model 154. In order to configure the second machine learning model 154 to return motion-artifact-only magnetic resonance imaging dataset, each second training set 158 may comprise a magnetic resonance imaging dataset and a motion-artifact-only magnetic resonance imaging dataset assigned to the respective magnetic resonance imaging dataset. The respective magnetic resonance imaging dataset may or may not comprise one or more motion artifacts. In case the respective magnetic resonance imaging dataset comprises no motion artifacts, the assigned motion-artifact-only magnetic resonance imaging dataset may comprise only zeros. In order to configure the second machine learning model 154 to return motion-artifact-corrected magnetic resonance imaging dataset, each second training set 158 may comprise a magnetic resonance imaging dataset and a motion-artifact-corrected magnetic resonance imaging dataset assigned to the respective magnetic resonance imaging dataset. The respective magnetic resonance imaging dataset may or may not comprise one or more motion artifacts. In case the respective magnetic resonance imaging dataset comprises no motion artifacts, the assigned motion-artifact-corrected magnetic resonance imaging dataset is identical with the respective magnetic resonance imaging dataset.

The second machine learning model 154 may be generated and/or configurated by executing the second learning algorithm 156 on the second training sets 158.

The analysis module 164 comprised by the computer memory 136 may further be configured to control the applying of the magnetic resonance imaging datasets 142.1, . . . , 142.N to the second machine learning model 154. Furthermore, the training module 166 may in addition contain computer executable code or instructions which enable the processor 130 to generate/configure the second machine learning model 154 using the second learning algorithm 156 in combination with the second training sets 158. In case the second machine learning model 154 is to be configured to return motion-artifact-only magnetic resonance datasets, the computer executable code or instructions of the motion artifact simulation module 168 may further enable the processor 130 to generate motion-artifact-only magnetic resonance imaging datasets with artificially calculated motion artifacts.

Figure 4:
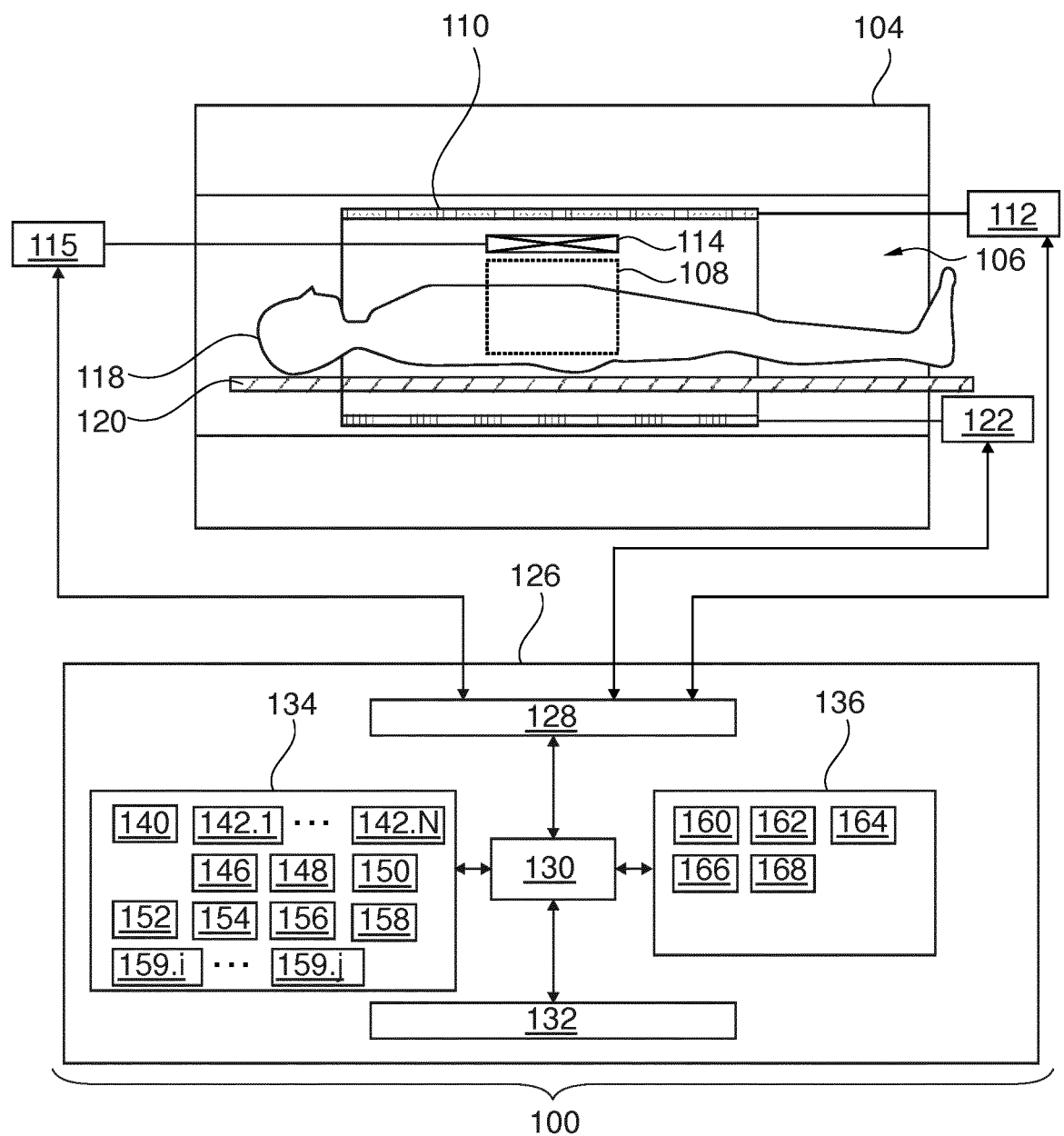
FIG. 4 illustrates a fourth example of a magnetic resonance imaging system.

FIG. 4 shows an example of an alternative embodiment of the magnetic resonance imaging system 100 of FIG. 2. In addition to the data objects shown in FIG. 2, the computer storage 134 of FIG. 3 further contains a second machine learning model 154 configured for filtering and/or correcting motion artifacts comprised by the magnetic resonance imaging datasets 142.1, . . . , 142.N representing 2D slices through the imaging zone 108. Applying the magnetic resonance imaging datasets 142.1, . . . , 142.N to the second machine learning model 154 results in artifact corrected magnetic resonance imaging datasets 159.*i*, . . . , 159.*j*. The magnetic resonance imaging datasets 142.1, . . . , 142.N may be provided to the second machine learning model 154 on default and the resulting artifact corrected magnetic resonance imaging datasets 159.*i*, . . . , 159.*j* may be provided to the first machine learning model 146. Alternatively, the magnetic resonance imaging dataset 142.1, . . . , 142.N may first be provided to the first machine learning model 146. In case the first machine learning model 146 detects a motion artifact in one of the magnetic resonance imaging datasets 142.1, . . . , 142.N, the respective a magnetic resonance imaging dataset 142.1, . . . , 142.N may be provided to the second machine learning model 154. According to embodiments, the resulting artifact corrected magnetic resonance imaging dataset 159.*i*, . . . , 159.*j* may also be provided to the first machine learning model 146 in order to check the success of the artifact correction and to monitor the contribution of the artifact corrected magnetic resonance imaging dataset 159.*i*, . . . , 159.*j* to the predicted motion artifact level. For example, the motion artifact correction may result in a motion artifact suppression, wherein still minor influences of the original motion artifacts remain.

Furthermore, the computer storage 134 may comprise a second learning algorithm 156 for generating/configuring the second machine learning model 154 using second training sets 158 as described above for the embodiment of FIG. 3.

Like in case of FIG. 2, the control module 160 may in contrast to the embodiments of FIG. 1 and FIG. 3 not be configured to combine the magnetic resonance imaging datasets 142.1, . . . , 142.N. The analysis module 164 comprised by the computer memory 136 may further be configured to control the applying of the magnetic resonance imaging datasets 142.1, . . . , 142.N to the second machine learning model 154. Furthermore, the training module 166 may in addition contain computer executable code or instructions which enable the processor 130 to generate/configure the second machine learning model 154 using the second learning algorithm 156 in combination with the second training sets 158.

Figure 5:
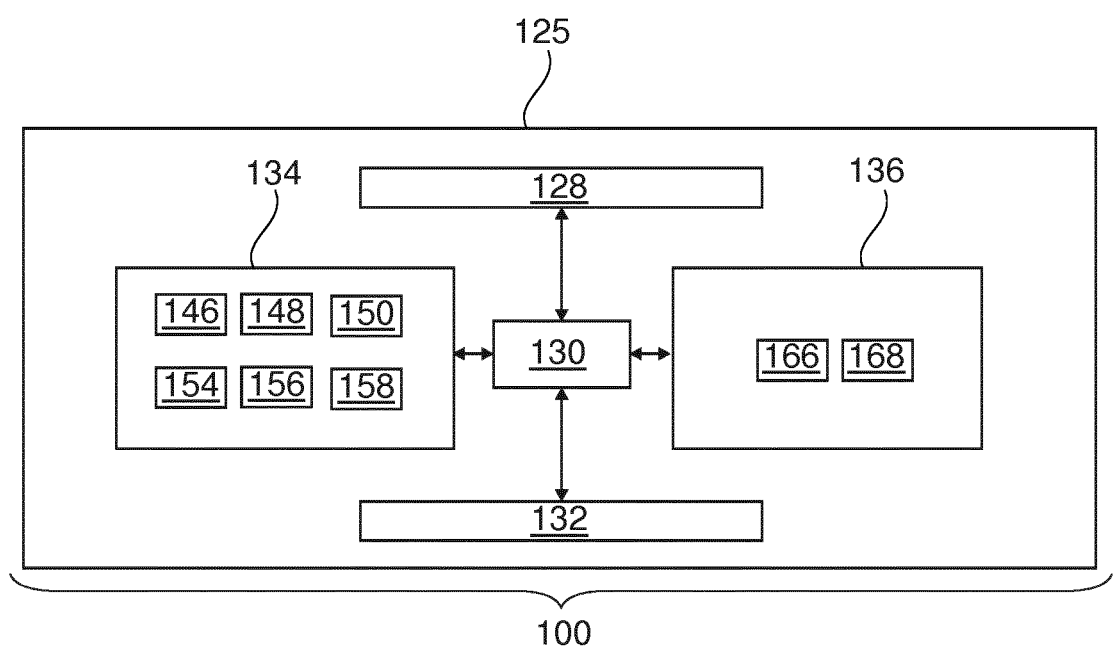
FIG. 5 illustrates an example of a computer system.

FIG. 5 shows an example of a computer 125 for generating the first machine learning model 146 and/or the second machine learning model 154 externally and provide the resulting machine learning models 146, 154 to a magnetic resonance imaging system 100, e.g. according to one of FIGS. 1 to 4. The computer 125 is shown to contain a hardware interface 128, a processor 130, a user interface 132, a computer storage 134 and a computer memory 136. The hardware interface 128 may e.g. be configured to provide the resulting machine learning models 146, 154 via a network to a magnetic resonance imaging system 100, e.g. according to one of FIGS. 1 to 4. The processor is configured to control the computer 125. The first machine learning model 146 shown in storage 134 may be generated/configured using a first learning algorithm 150 and first training sets 152 as exemplarily described above for the embodiments of FIG. 1 and FIG. 2. The second machine learning model 154 shown in storage 134 may be generated/configured using a second learning algorithm 156 and second training sets 158 as exemplarily described above for the embodiments of FIG. 3 and FIG. 4.

The training module 166 may contain computer executable code or instructions which enable the processor 130 to generate/configure the first machine learning model 146 using the first learning algorithm 150 in combination with the first training sets 152 and/or second machine learning model 154 using the second learning algorithm 156 in combination with the second training sets 158. The computer memory 136 may further comprise a motion artifact simulation module 168 containing computer executable code or instructions. The computer executable code or instructions of the motion artifact simulation module 168 enable the processor 130 to generate magnetic resonance imaging datasets with artificially calculated motion artifacts for the first training sets 152 and/or the second training sets 158 by simulating and introducing varying numbers, extents and/or types of artificially generated motion artifacts to one or more motion-artifact-free magnetic resonance images. In case the second machine learning model 154 is to be configured to return motion-artifact-only magnetic resonance datasets, the computer executable code or instructions of the motion artifact simulation module 168 may further enable the processor 130 to generate motion-artifact-only magnetic resonance imaging datasets with artificially calculated motion artifacts.

Figure 6:
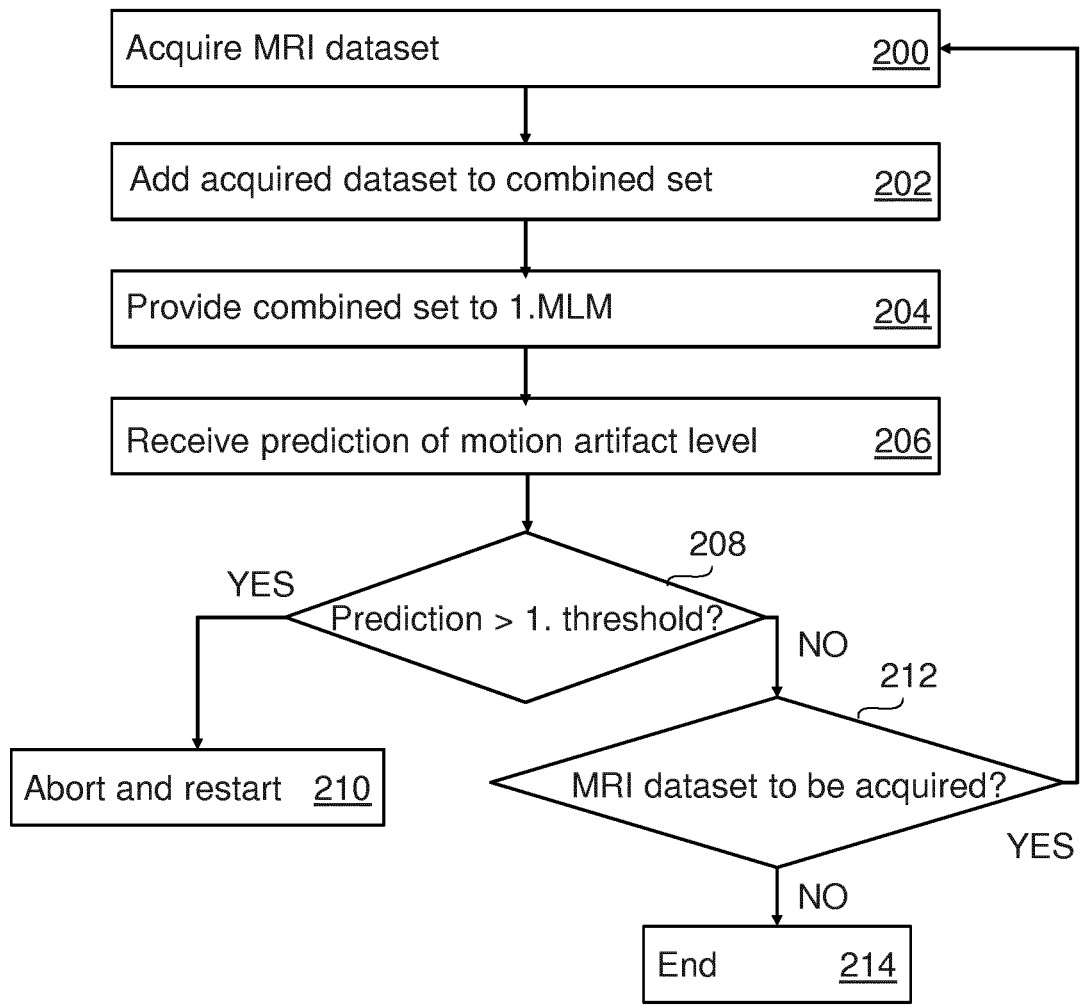
FIG. 6 illustrates an example of a method of operating the magnetic resonance imaging system of FIG. 1.

FIG. 6 shows a schematic flowchart which illustrates a method of operating the magnetic resonance imaging system 100 of FIG. 1. The acquisition and analysis process according to the steps shown may be repeatedly performed until the complete set of MRI data to be acquired according to the pulse sequence commands has been acquired by the MRI system 100. The acquisition of the set of MRI data is split up into an acquisition of a plurality of MRI datasets, each comprising a subset of the set of MRI data to be acquired. In this embodiment, the set of MRI data is acquired operating the MRI system in a 3D operating mode. The acquisition and analysis process starts with step 200. In step 200, an MRI dataset is acquired from an imaging zone of the magnetic resonance imaging system according to the pulse sequence commands. In step 202, the acquired MRI dataset is added to a combined set of MRI data acquired so far. In step, 204, the combined set of MRI data is provided to the first input of the first machine learning model (MLM). The combined set of MRI data may comprise the acquired MRI data either in k-space representation or in form of a magnetic resonance image reconstructed from the respective MRI data. In step 206, a prediction of a motion artifact level of the acquired magnetic resonance imaging data, i.e. of the combined set of MRI data, is received from the first output of the first machine learning model. The motion artifact level characterizes a number and/or extent of motion artifacts present in the combined set of MRI data provided to the first machine learning model. In step 208, it is checked whether the received prediction of the motion artifact level exceeds a first threshold. The first threshold is for example defined as a maximum motion artifact level which is considered to be acceptable in order to be able to use the acquired MRI data for diagnostic purposes. In case the first threshold is exceeded, it is indicated that the combined set of MRI data comprises motion artifact levels which number and/or extent are so large that the combined set of MRI data is not suitable e.g. for diagnostic purposes. In case the first threshold is exceeded, the further MRI data acquisition and analysis is aborted in step 210, since the data acquired so far has an insufficient quality in view of motion artifacts.

In case the first threshold is not exceeded, the method continues with step 212. In step 212, it is checked whether all MRI datasets to be acquired according to the pulse sequence commands have been acquired. In case the latest MRI dataset acquired is the last MRI dataset to be acquired, the method ends with step 214. In case there are one or more MRI datasets to be acquired according to the pulse sequence command, the method continues with step 200. In other words, the acquisition and analysis process is performed once again. The acquisition and analysis process is repeatedly performed until all of the MRI datasets to be acquired have been acquired or until the data acquisition is aborted due to a lack of quality of the MRI data acquired so far.

Figure 7:
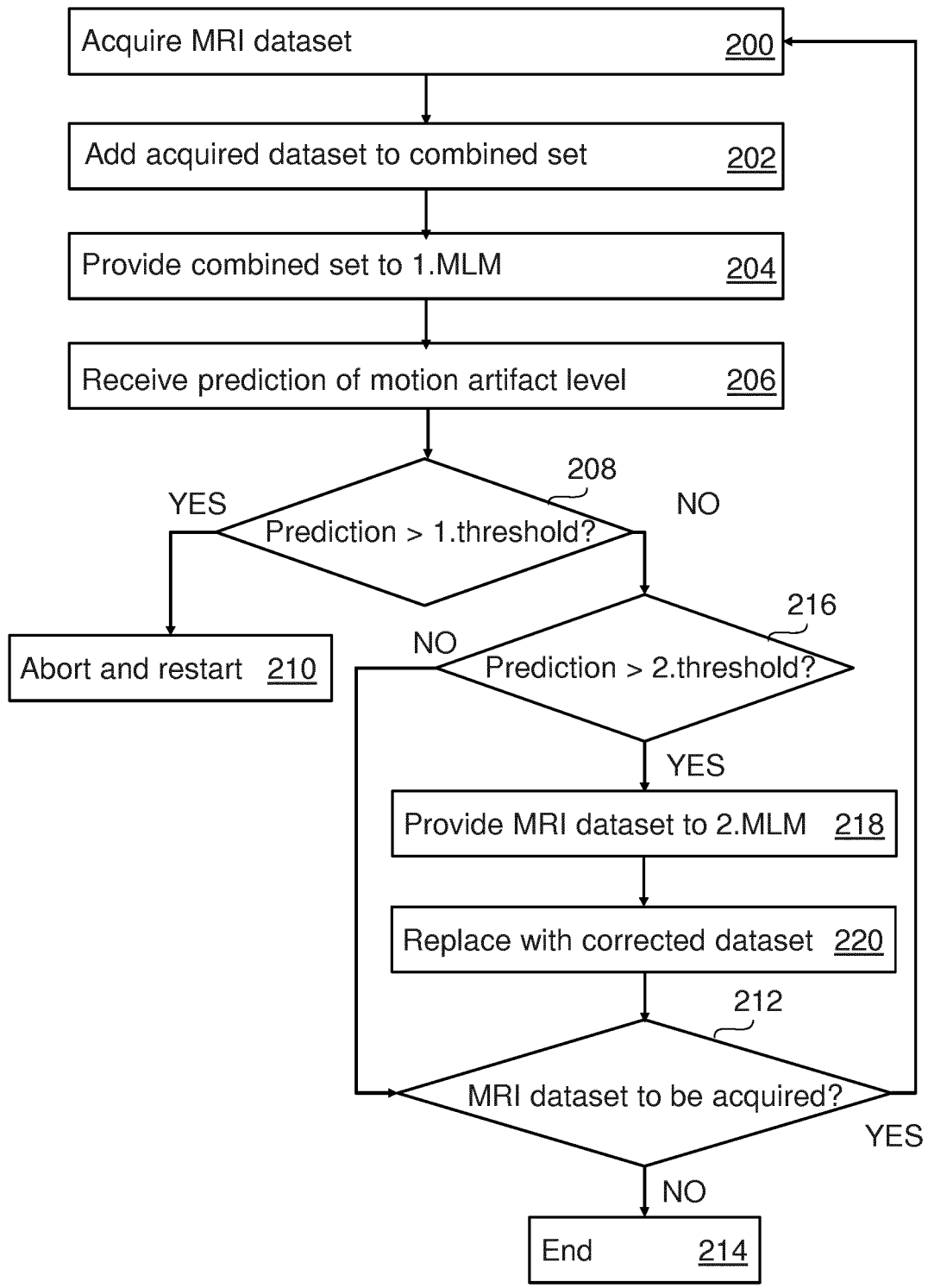
FIG. 7 illustrates an example of a method of operating the magnetic resonance imaging system of FIG. 3.

FIG. 7 shows a schematic flowchart which illustrates a method of operating the magnetic resonance imaging system 100 of FIG. 3. In addition to the steps illustrated in FIG. 6, the method of FIG. 7 further comprises steps 216 to 220 related to the second machine learning model. The second machine learning model is configured to correct motion artifacts comprised by MRI datasets provided to second input of the second machine learning model. In step 216, it is checked whether the prediction of the motion artifact level exceeds a second threshold. The second threshold may e.g. be provided in form of a motion artifact level smaller than the first threshold or in form of a relative threshold. Such a relative threshold may define a maximal increase of the prediction of the motion artifact level due to taking into account the latest MRI dataset, which is considered to be acceptable. In other words, the second threshold may be a threshold for the contribution of the latest MRI datasets to the prediction of the motion artifact level. In case the second threshold is zero, it may be exceeded whenever the latest MRI dataset comprises any motion artifact corrupted data. When the second threshold is larger than zero, a certain contribution of each MRI dataset to the motion artifact level is considered to be acceptable.

In case the second threshold is not exceeded, the method may continue with step 212. Else, the method may continue with step 218, in which the MRI dataset is provided to the second input of the second machine learning model. Using the reply from the second output of the second machine learning model, a motion-artifact-corrected MRI dataset is provided which replaces the MRI dataset provided to the second machine learning model. In other words, the motion-artifact-corrected MRI dataset is added to the combined set of MRI data, while the replaced MRI dataset is subtracted from the combined set of MRI data. Then, the method may continue with step 212. Alternatively, steps 204 to 208 may be repeated in order to check whether the effect of the replacement with the motion-artifact-corrected MRI dataset.

The reply from the second output of the second machine learning model may either be the motion-artifact-corrected MRI dataset itself or a motion-artifact-only MRI dataset comprising only the one or more motion artifacts comprised by the MRI dataset provided to the second input. The motion-artifact-only MRI dataset may then be subtracted from the MRI dataset provided to the second input resulting in the desired motion-artifact-corrected MRI dataset.

Figure 8:
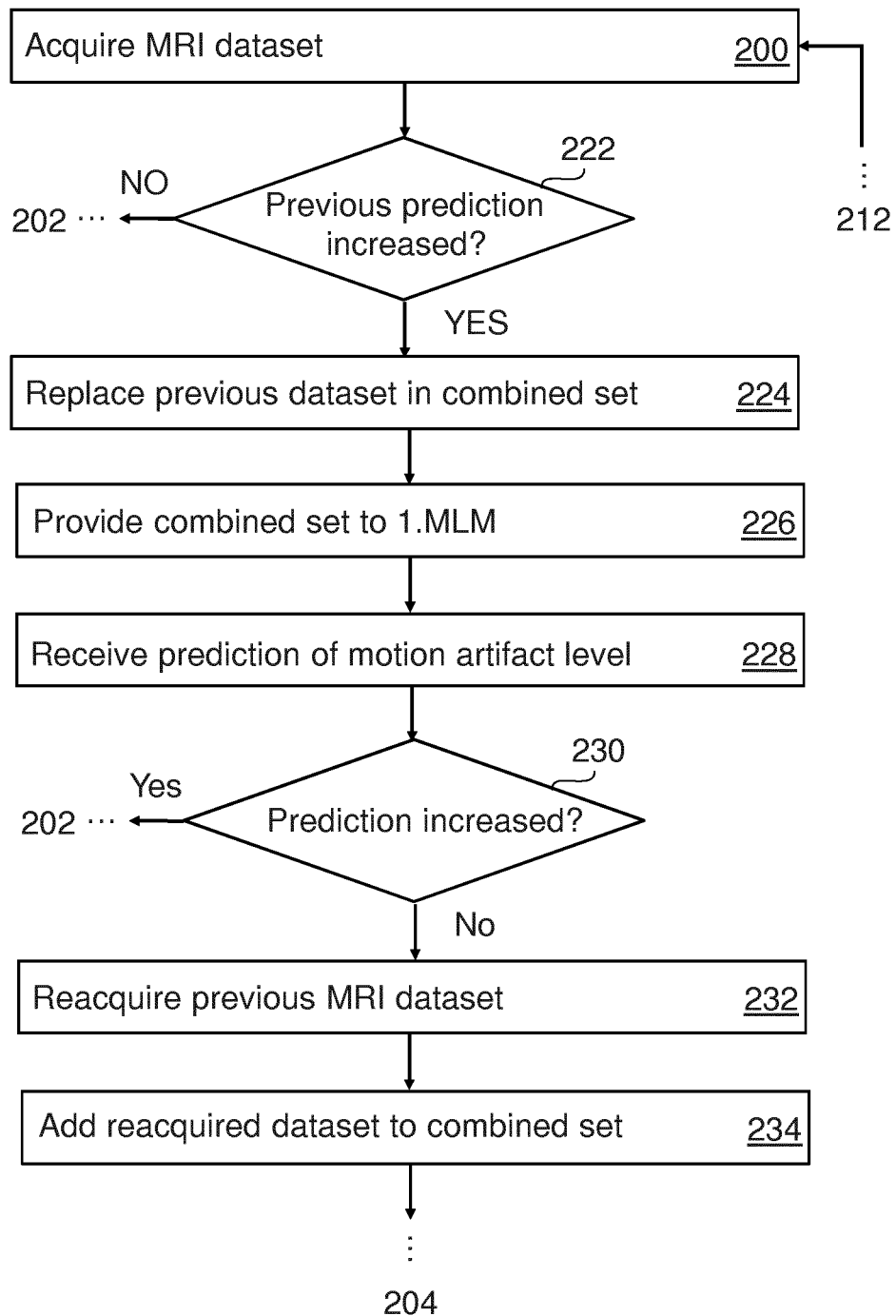
FIG. 8 illustrates an example of a method of operating the magnetic resonance imaging system of FIG. 3.

FIG. 8 shows a schematic flowchart which illustrates optional additional steps for the methods of FIG. 6 and FIG. 7. The additional steps comprise steps 222 to 234. In step 222, it is checked whether the prediction of the motion artifact level received in the last preceding repetition of the acquisition and analysis process has been increased relative to the prediction of the motion artifact level received in the second to last preceding repetition of the acquisition and analysis process. If this is the case, the method may continue with step 224, else with step 202. In step 224, the MRI dataset acquired in the last preceding repetition of the acquisition and analysis process is replaced in the combined set of MRI data by the MRI dataset acquired in the current repetition in step 200. In other words, the MRI dataset acquired in the last preceding repetition of the acquisition and analysis process is subtracted from the combined set of MRI data, i.e. omitted, while the MRI dataset acquired in the current repetition in step 200 is added to the combined set of MRI data. In step 226, the resulting combined set of MRI data is provided to the first machine learning model. In step 228, a prediction of the motion artifact level is received. In step 230, it is checked whether the prediction of the motion artifact level received in step 228 of the current repetition is increased relative to the prediction of the motion artifact level received in the second to last preceding repetition as well. If this is the case, the motion artifact causing the increase detected in step 222 is not restricted to the MRI dataset acquired in the last preceding repetition. The method may continue with step 202. If this is not the case, the method may continue with step 232. In step 232 the MRI dataset acquired in the last preceding repetition may be re-acquired. Since it has been determined that the motion artifact was restricted to the MRI dataset acquired in the last preceding repetition, it follows that the patient has returned to the original position. In step 234, the re-acquired MRI data may be added to the combined set of MRI data amended in step 224. Thus, the MRI dataset acquired in the last preceding repetition which has been eliminated from the combined set in step 224 is omitted.

Figure 9:
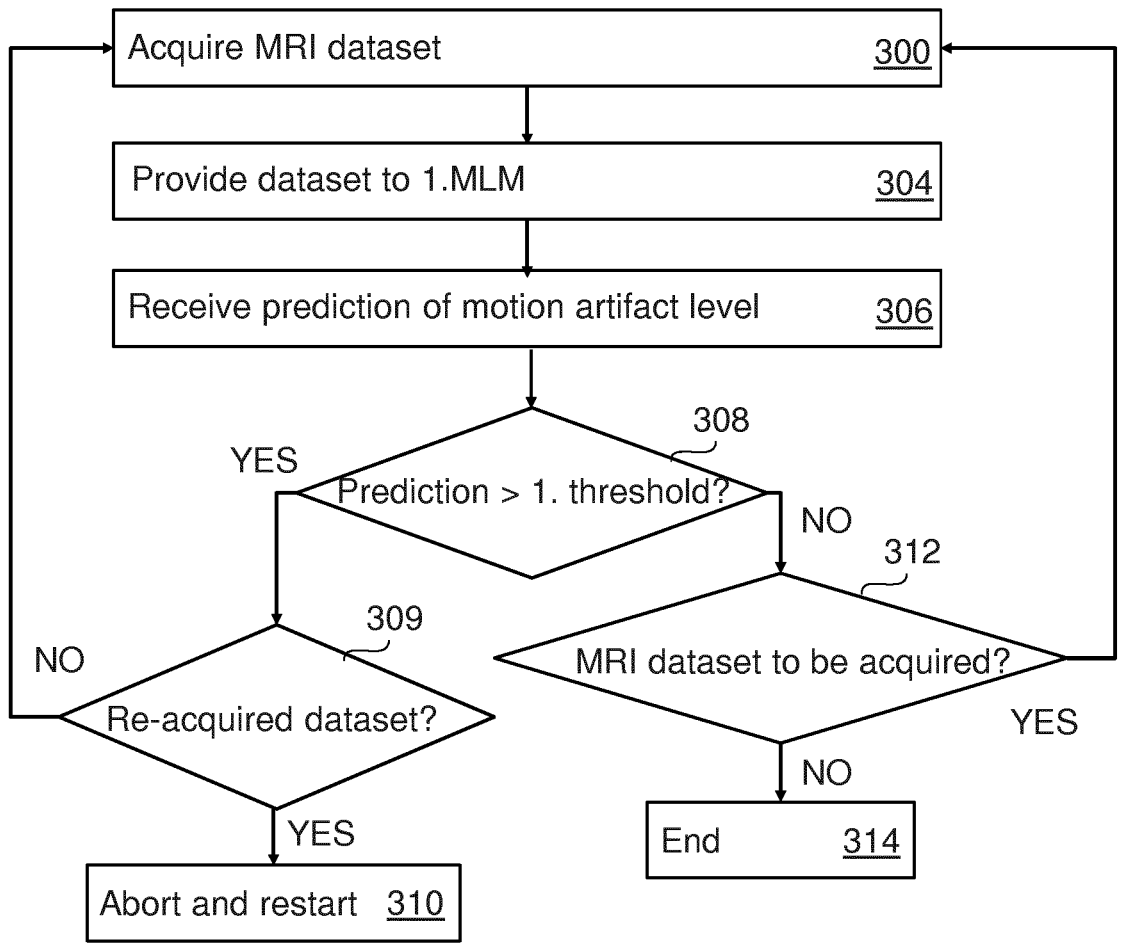
FIG. 9 illustrates an example of a method of operating the magnetic resonance imaging system of FIG. 2.

FIG. 9 shows a schematic flowchart which illustrates a method of operating the magnetic resonance imaging system 100 of FIG. 2. The method of FIG. 9 is highly similar to the method of FIG. 6. The main difference is that the magnetic resonance imaging system 100 in case of FIG. 9 is not operated in the 3D mode anymore, but rather in the multi-2D mode. In other words, the acquired MRI datasets may each comprise MRI data of an individual 2D slice through the imaging zone, resulting in a stack of parallel 2D slices. Each of the 2D slices may be analyzed individually. Step 300 of FIG. 9 corresponds to step 200 of FIG. 6, while steps 304 to 314 of FIG. 9 correspond to steps 204 to 214 of FIG. 6. The main difference of the method of FIG. 6 in comparison with the method according to FIG. 9 is that the 2D slices and thus the acquired MRI datasets are not combined with each other, but rather are individually provided to the first input of the first machine learning model. Thus, each of the MRI datasets is analyzed individually. In step 308, it may be checked that none of the predictions of any of the MRI datasets exceeds the first threshold. Alternatively, an average value of the predictions of the motion artifact level may be calculated and compared with the first threshold. In case the first threshold is exceeded, it may be checked in step 309, whether the current MRI dataset is the result of a re-acquisition limited to this particular MRI dataset, i.e. the corresponding sampling points. In case the current MRI dataset is the result of a limited re-acquisition attempt, the method may continue with step 310 and a restart. The restart may result in a re-acquisition of all the MRI datasets to be acquired according to the pulse sequence commands. In case the current MRI dataset is not the result of a limited re-acquisition attempt, such a limited re-acquisition attempt for the current MRI dataset may be performed by continuing with step 300 for the current MRI dataset. This may have the beneficial effect that not all the MRI datasets have to be re-acquired due to a restart, but that the re-acquisition may be limited to single MRI dataset.

Figure 10:
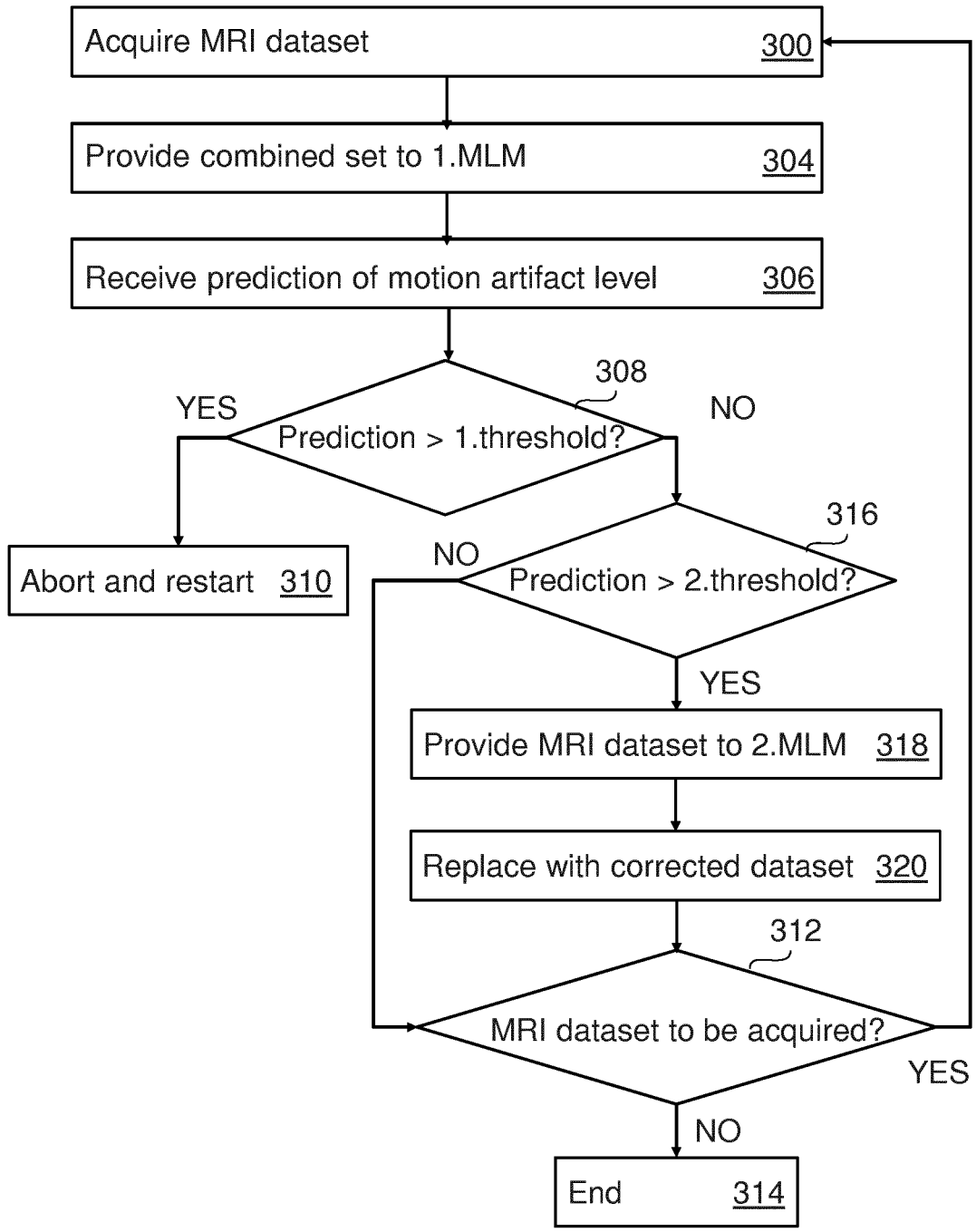
FIG. 10 illustrates an example of a method of operating the magnetic resonance imaging system of FIG. 4.

FIG. 10 shows a schematic flowchart which illustrates a method of operating the magnetic resonance imaging system 100 of FIG. 4. The method of FIG. 10 is highly similar to the method of FIG. 7. Like in case of the method of FIG. 9, the MRI system executing the method of FIG. 10 is operated in the multi-2D mode. Thus, all the acquired MRI datasets may comprise data of an individual 2D slice. Step 300 of FIG. 9 corresponds to step 200 of FIG. 7, while steps 304 to 314 of FIG. 10 correspond to steps 204 to 214 of FIG. 7. Furthermore, steps 316 to 320 of FIG. 10 correspond to steps 216 to 220 of FIG. 7.

Figure 11:
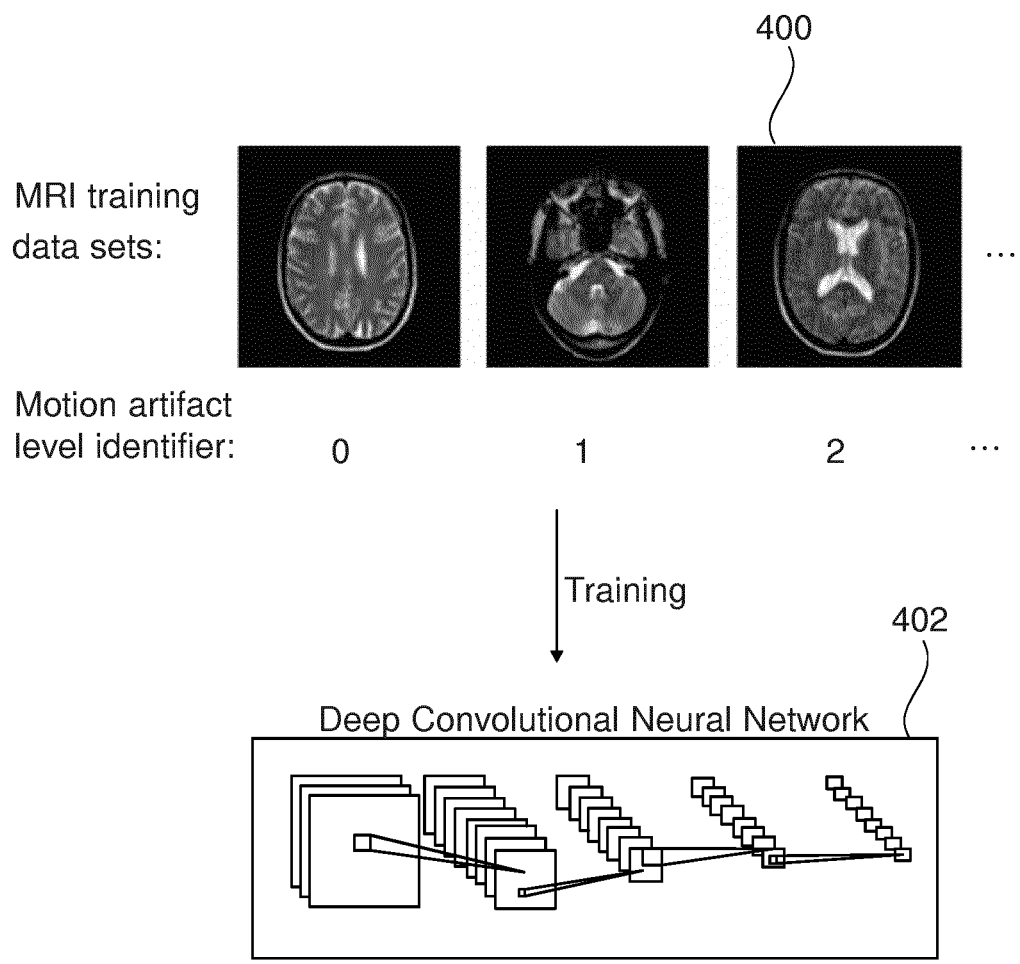
FIG. 11 illustrates an example of a method of training a deep learning network for motion artifact level determination.

FIG. 11 shows a schematic flowchart which illustrates a method for generating the first machine learning model using the first training algorithm. The first machine learning mode comprises a deep convolutional neural network 402, like e.g. a deep convolutional neural network. Training refers to an optimization of the weights and biases of the neurons comprised by the deep convolutional neural network to achieve desired capabilities for detecting the presence of motion artifacts in magnetic resonance imaging datasets and determining a motion artifact level, i.e. classify the respective motion artifacts. The training may comprise providing a large number of first training sets 400 of clinical magnetic resonance imaging datasets with and without motion artifacts. Each of the clinical magnetic resonance imaging datasets is assigned with a motion artifact level identifier identifying the artifact level of the respective imaging datasets. FIG. 11 illustrates an exemplary definition of the motion artifact levels by a single integer number in the range from 0 to 2, which may represent imaging datasets with no (0), mild (1) or severe motion artifacts (2), respectively. In a training phase, the clinical magnetic resonance imaging datasets provided by the first training sets 400 are applied as input to an untrained deep learning network, like e.g. a deep convolutional neural network. The deep convolutional neural network returns motion artifact level identifier as output which may be compared with the motion artifact level identifier assigned to the clinical magnetic resonance imaging datasets applied as input. This may be performed for batches comprising a plurality of the clinical magnetic resonance imaging datasets and the differences may be statistically evaluated by the first training algorithm. Based on these evaluation parameters the deep convolutional neural network may be adjusted until the output provided by the deep convolutional neural network, when applying the clinical magnetic resonance imaging datasets of the first training sets 400 to the same, correspond to the motion artifact level identifier assigned to the respective datasets. The training results in a trained deep convolutional neural network 402 which may be used for determining motion artifact level, like e.g. shown in FIG. 12.

Figure 12:
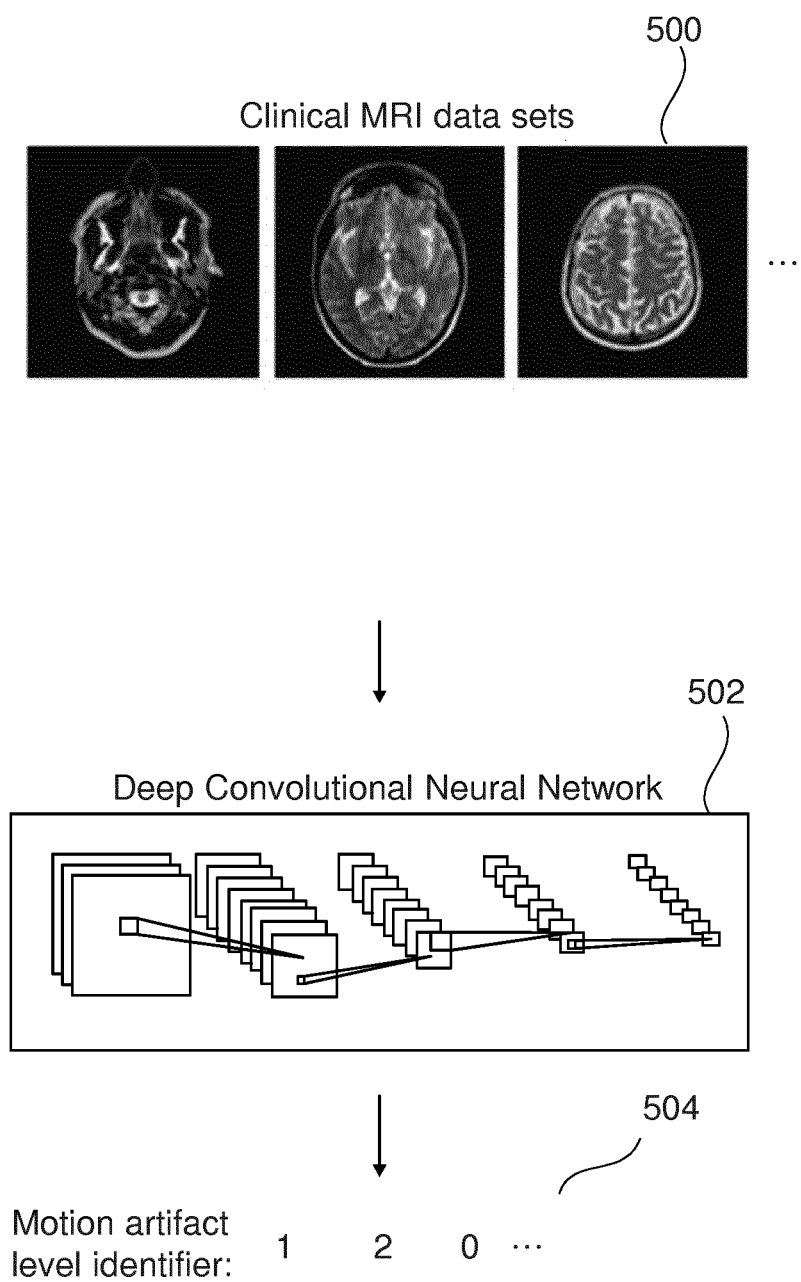
FIG. 12 illustrates an example of a method of motion artifact level determination using a trained a deep learning network.

FIG. 12 shows a schematic flowchart which illustrates a method of using the first machine learning model. Clinical magnetic resonance imaging datasets 500 are acquired. The clinical magnetic resonance imaging datasets are provided to first input of the first machine learning model comprising a trained deep convolutional neural network 502, which may have been trained according to FIG. 11. As a result, predictions of motion artifact levels 504 may be received from the first output of the first machine learning model.

Figure 13:
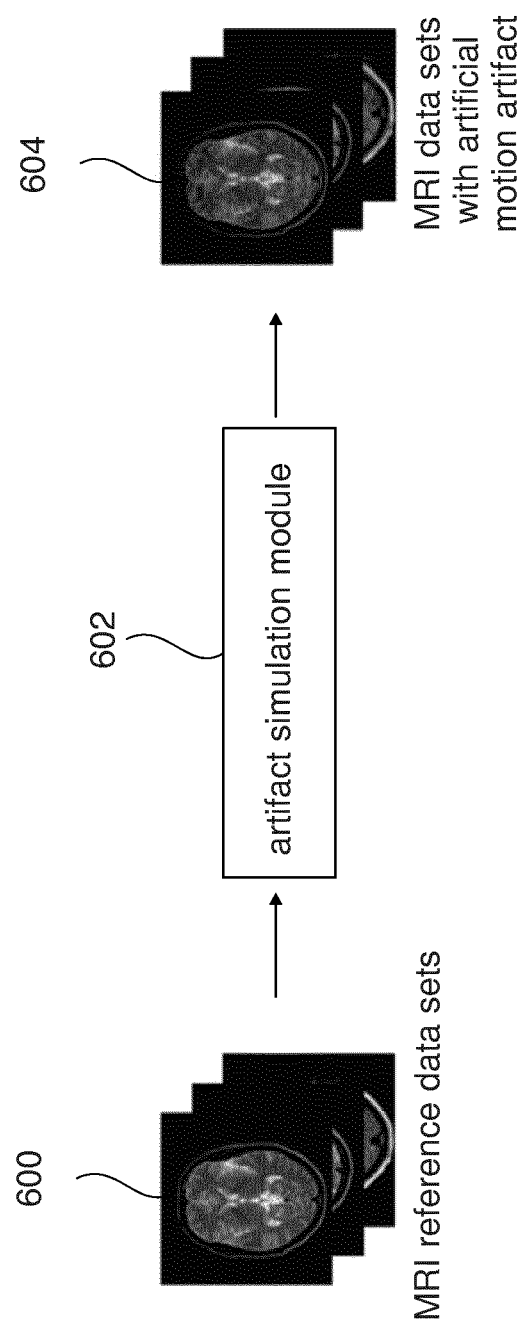
FIG. 13 illustrates an example of a method of generating MRI datasets with artificial motion artifacts.

FIG. 13 shows a schematic flowchart which illustrates a method for generating magnetic resonance imaging datasets with motion artifacts for the first and/or second training sets. A set of motion-artifact-free magnetic resonance imaging datasets 600 is provided. The motion-artifact-free magnetic resonance imaging datasets may furthermore be used as magnetic resonance imaging reference datasets, e.g. for training a fully convolutional neural network for filtering motion artifacts present in magnetic resonance imaging datasets. The motion-artifact-free magnetic resonance imaging datasets 600 are applied to a motion artifact simulation module 602 generating artificial motion artifacts. By introducing the artificial motion artifacts to motion-artifact-free magnetic resonance imaging datasets 600, magnetic resonance imaging datasets 604 with one or more motion artifacts are generated. The magnetic resonance imaging datasets 604 may each be paired with the motion-artifact-free magnetic resonance imaging datasets 600 used to generated the respective magnetic resonance imaging datasets 604, in order to generate the second training sets. Alternatively, the simulated motion artifacts may be stored in form of motion-artifact-only magnetic resonance datasets. The motion-artifact-only magnetic resonance datasets may each be paired with the motion-artifact-free magnetic resonance imaging datasets 600 used to generated the respective magnetic resonance imaging datasets 604, in order to generate the second training sets. The magnetic resonance imaging datasets 604 may each be assigned with a motion artifact level identifier identifying the motion artifact level of the respective magnetic resonance imaging datasets due to the one or more motion artifacts introduced by the motion artifact simulation module 602, in order to generate the first training sets.

Figure 14:
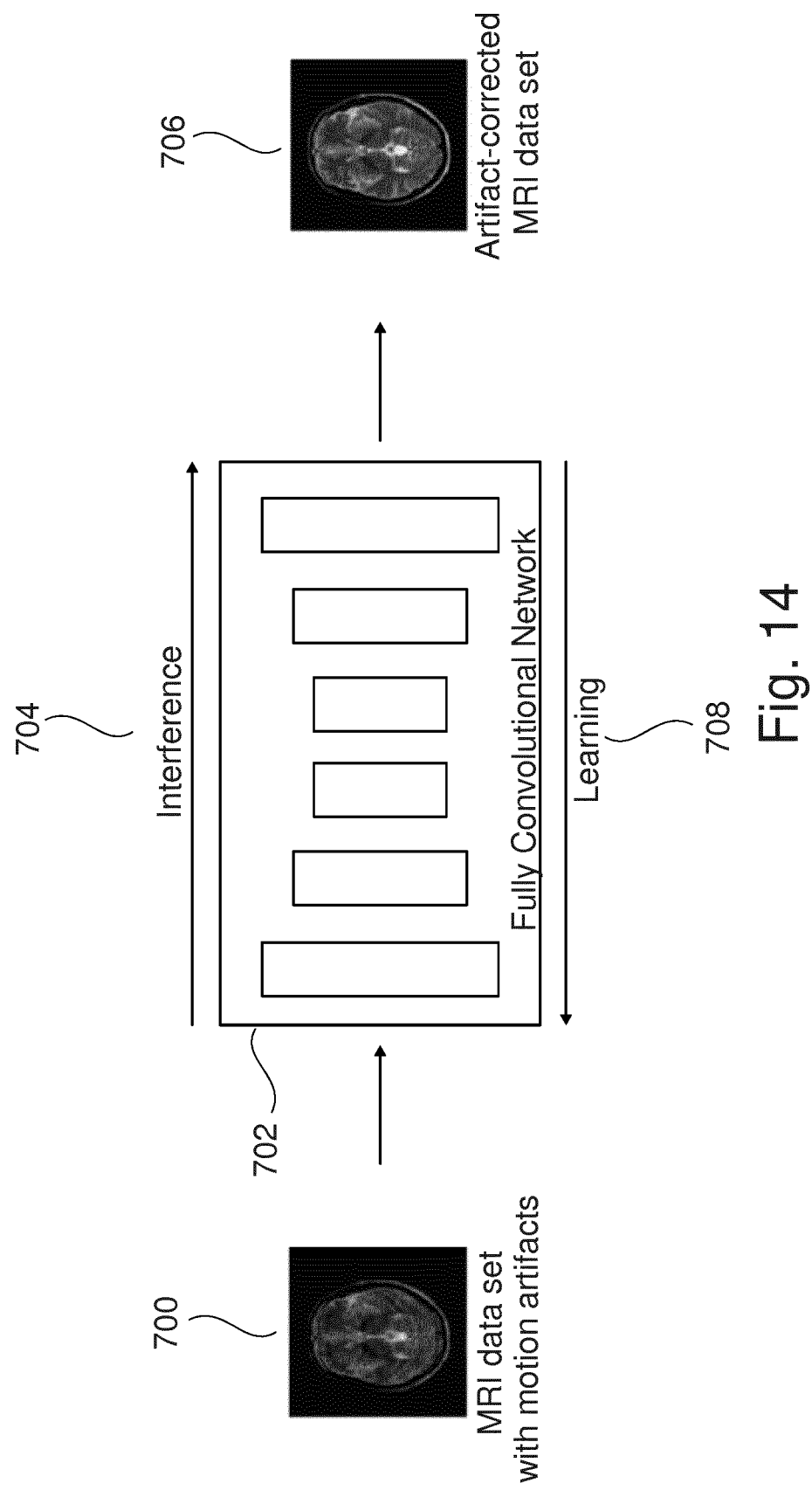
FIG. 14 illustrates an example of a method of training a deep learning network for motion artifact correction.

FIG. 14 shows a schematic flowchart which illustrates a method for training a second machine learning model comprising a fully convolutional neural network 702. During an iterative process execution by the second learning algorithm, the network parameters of the fully convolutional neural network 702 may be optimized. In an inference step 704, a prediction of a motion-artifact-corrected magnetic resonance imaging dataset 706 may be generated by the fully convolutional neural network 702 using a magnetic resonance imaging dataset with motion artifacts 700 provided by a second training set. The resulting difference between a motion-artifact-free imaging reference dataset of the second training set and the output of the fully convolutional neural network 702 is propagated back through the respective fully convolutional neural network 702 during a learning phase 708. This procedure may for example be performed by applying batches of resonance imaging datasets with motion artifacts 700 provided by second training sets to the fully convolutional neural network 702 and statistically evaluating the differences between the input batch and a resulting output batch comprising a plurality of predictions of motion-artifact-corrected magnetic resonance imaging datasets 706. After a successful training, the fully convolutional neural network 702 may be provided with actual motion-artifact-corrupted magnetic resonance imaging datasets and may return magnetic resonance imaging datasets with reduced artifact level as a result. According to alternative embodiments, the second training sets may comprise motion-artifact-only magnetic resonance datasets instead of the motion-artifact-corrected magnetic resonance imaging datasets 706 and the second machine learning model may be trained, i.e. configured, to predict motion-artifact-only magnetic resonance datasets.

Figure 15:
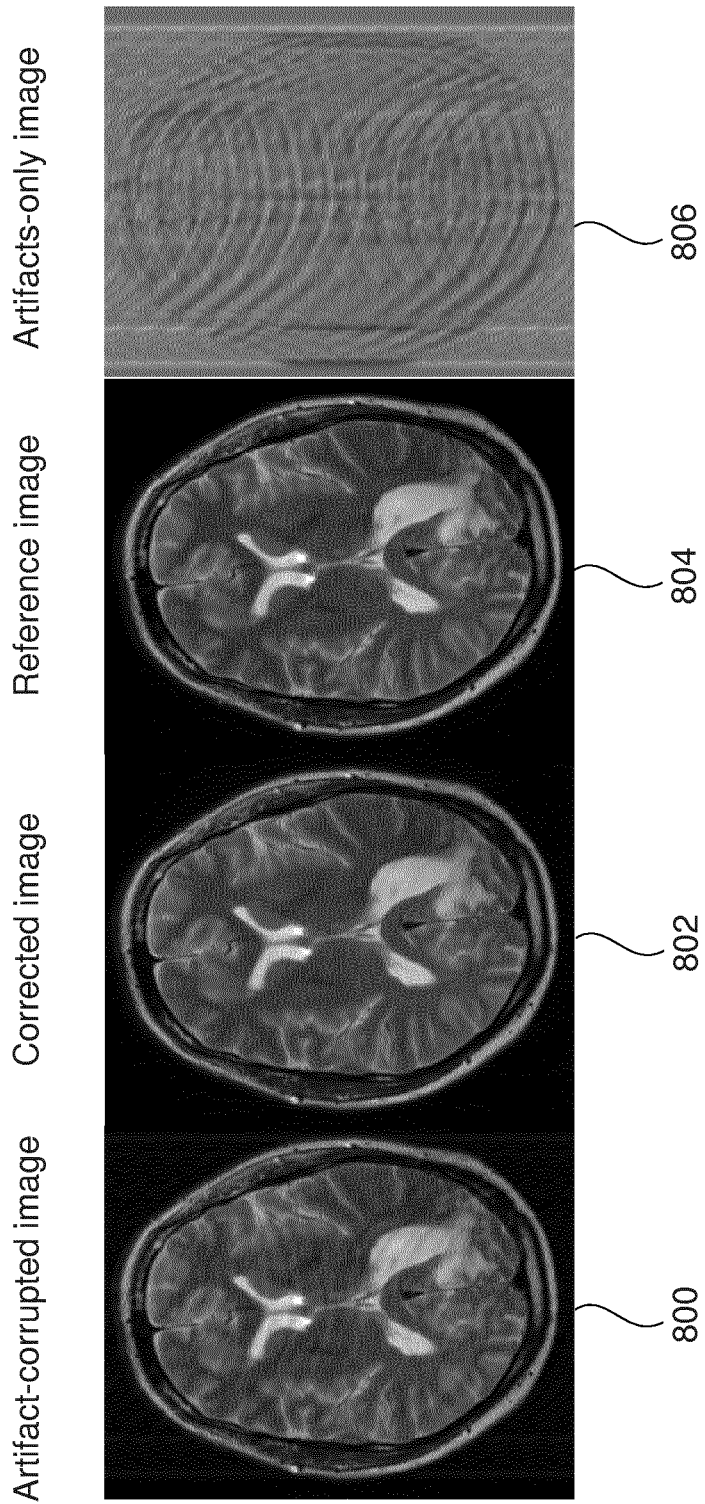
FIG. 15 illustrates an example of MRI images used for motion artifact correction.

FIG. 15 shows an exemplary magnetic resonance reference image 804 without motion artifacts. Reference image 804 is provided by a magnetic resonance imaging reference dataset representing an exemplary slice through a set of magnetic resonance imaging data. In addition, an exemplary magnetic resonance image 800 is shown which comprises artificial motion artifacts and may be provided to the second input of the second machine learning model. Reference image 804 is provided in order to illustrate the effectiveness of the processing of the motion artifacts present in the magnetic resonance image 802 using the second machine learning model. Furthermore, a motion-artifact-corrected magnetic resonance image 802 is shown. Motion-artifact-corrected magnetic resonance image 802 results from a correction of motion-artifact-corrupted magnetic resonance images 800. The motion-artifact-corrected magnetic resonance image 802 may be provided directly by the second output by second machine learning model. Alternatively, the second machine learning model may be configured to return motion-artifact-only magnetic resonance images. An example of such a motion-artifact-only magnetic resonance image is illustrated by magnetic resonanc image 806. In case, the fully convolutional neural network returns a motion-artifact-only magnetic resonance image 806 at the second output, the motion-artifact-corrected magnetic resonance image 802 may be generated by subtracting motion-artifact-only magnetic resonance image 806 from the original magnetic resonance images 800 comprising the motion artifacts represented by the motion-artifact-only magnetic resonance image 806.

The generation and usage of the images 800 to 806 may be further illustrated in the following. For example, a reference image 804 is acquired based on T2-weighted whole-brain patient scans with multi-2D spin echo sequence and magnitude data only. The reference image 804 may be reconstructed from acquired magnetic resonance imaging data rated as motion-artifact-free. Artifacts due to bulk translational motion may be simulated for the reference image 804 by an additional phase that is applied to the Fourier transformed data:

$$\tilde{S}(\vec{k}) = S(\vec{k}) e^{i 2\pi \vec{k} \cdot \vec{T}},$$

where T defines the motion trajectory. Three different translational trajectories, i.e. sudden, oscillating, and continuous motion, may be simulated with varying motion amplitudes in the range of e.g. 2 to 12 pixels. Furthermore, artifacts due to bulk rotational motion may be simulated for reference image 804 by replacing parts of the Fourier transformed input image by the Fourier transform of a rotated version of the input image. Two different rotational trajectories, i.e. sudden and oscillating motion, may be simulated with varying motion amplitudes e.g. in the range of 1.0° to 2.5°.

To increase the anatomic variability furthermore, random deformation, may be applied to the reference image 804. The motion-artifact-only image 806 may be returned by the second machine learning model. In total, training sets comprising image pairs in the order of 100,000, each comprising a motion-artifact-corrupted image 800 and a reference image 804, may be generated using unique patient whole-brain scans of the order of 10. Using two additional T2-weighted whole-brain scans, a training set consisting of 100 images may be generated in the same way.

The fully convolutional neural network of a second machine learning model may for example be implemented relying on a multi-resolution approach, i.e. two downsampled variants of the input image are used as additional inputs to the fully convolutional network. Each resolution level may consist of two convolutional layers, each followed by a batch normalization layer and a rectifier linear unit. The different levels may be combined using average-un-pooling layers and shortcut connections. The fully convolutional neural network may be trained to minimize the mean square error between predicted motion artifacts and simulated motion artifacts. Training may e.g. be carried out during 32 epochs using the Adam optimization method and a mini-batch size of 32.

Afterwards, the trained fully convolutional neural network of the second machine learning model may be applied to a testing sets. The testing sets may correspond to the training sets. Motion-artifact-corrupted images 800 may be provided to the second input to the second machine learning model and predictions of the artifacts, i.e. motion-artifact-only images 806, may be returned from the second output. The motion-artifact-only images 806 may be subtracted from the motion-artifact-corrupted input images 800, resulting in the motion-artifact-corrected magnetic resonance images 802. The resulting motion-artifact-corrected magnetic resonance images 802 may be compared with the magnetic resonance reference images 804.

Figure 16:
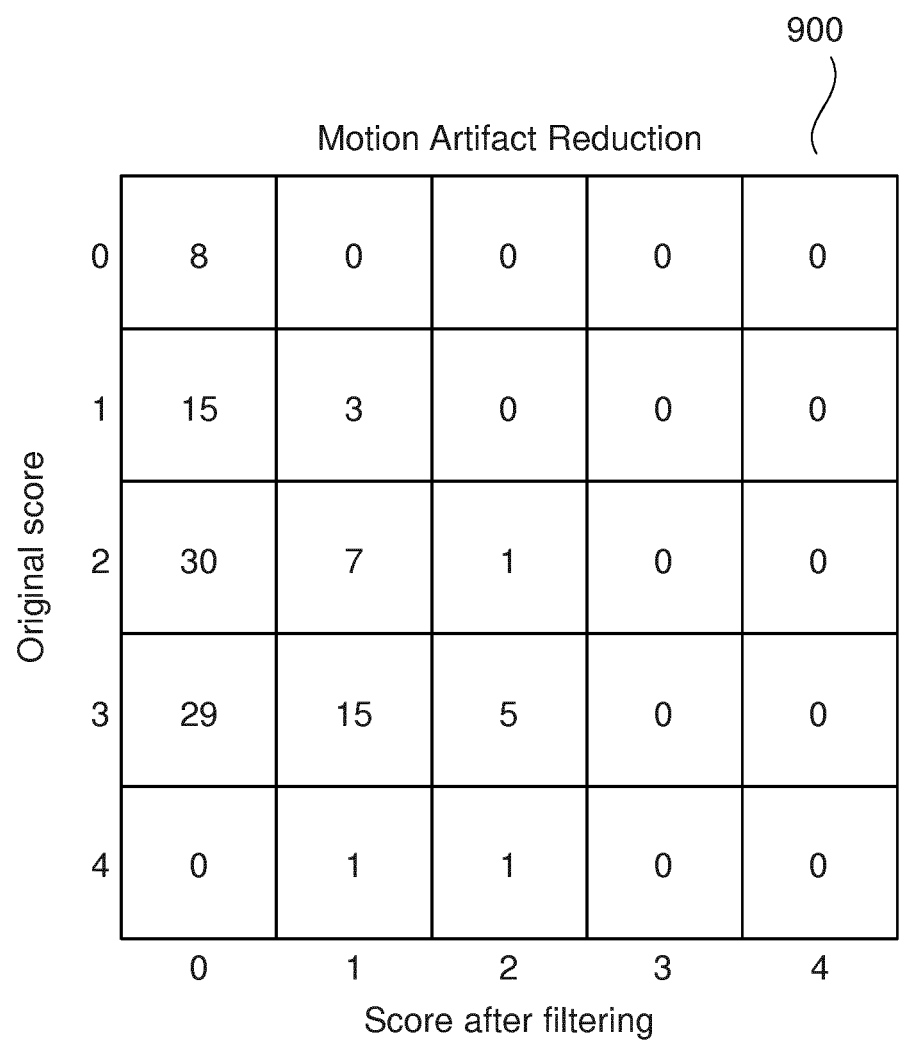
FIG. 16 illustrates results of motion artifact correction.

FIG. 16 illustrates the results of the aforementioned filtering given in terms of a confusion matrix 900. Confusion matrix 900 illustrates the success of the motion artifact reduction by comparing the numbers of motion-artifact-corrupted images 800 per class 0 to 4 before applying the same to the second machine learning model with the numbers motion-artifact-corrected magnetic resonance image 802 per class 0 to 4 after application to the second machine learning model with a trained fully convolutional neural network. The artifacts may e.g. be classified using a five-point Likert scale. The comparison shows, that on average an improvement of 1.8 point has been achieved, while no additional quality degeneration is observable. For the majority of the slices, the application of the filter provided by the fully convolutional neural network resulted in a considerable reduction of the perceived severity, with an average improvement of around 1.8 points.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 magnetic resonance imaging system
104 main magnet
106 bore of magnet
108 imaging zone
110 magnetic field gradient coil
112 magnetic field gradient coil power supply
114 radio-frequency coil
115 transceiver
118 subject
120 subject support
122 actuator
125 computer
126 computer 128 hardware interface
130 processor
132 user interface
134 computer storage
136 computer memory
140 pulse sequences
142.1, ..., 142.2 MRI dataset
144 combined set of MRI data
146 first machine learning model
148 results
150 first learning algorithm
152 first training sets
154 second machine learning model
156 second learning algorithm
158 second training sets
159.i, ..., 159.j corrected MRI dataset
160 control module
162 imaging reconstruction module
164 analysis module
166 training module
168 motion artifact simulation module
400 MRI training sets
402 deep convolutional neural network
500 clinical MRI datasets
502 trained deep convolutional neural network
504 motion artifact level identifier
600 MRI reference datasets
602 artifact simulation module
604 MRI datasets with artificial motion artifacts
700 MRI datasets with motion artifacts
702 fully convolutional neural network
704 inference phase
706 motion-artifact-corrected MRI datasets
708 learning phase
800 motion-artifact-corrupted input image
802 motion-artifact-corrected image
804 reference image
806 motion-artifacts-only image
900 confusion matrix

The invention claimed is:

1. A magnetic resonance imaging system, the magnetic resonance imaging system comprising:
a non-transitory memory storing machine executable instructions, pulse sequence commands and a first machine learning model comprising a first deep learning network, wherein the pulse sequence commands are configured for controlling the magnetic resonance imaging system to acquire a set of magnetic resonance imaging data, wherein the first machine learning model comprises a first input and a first output; and
a processor, wherein execution of the machine executable instructions causes the processor to control the magnetic resonance imaging system to repeatedly perform an acquisition and analysis process, wherein for each current repetition, the acquisition and analysis process comprises:
    acquiring a current dataset comprising a subset of the set of magnetic resonance imaging data from an imaging zone of the magnetic resonance imaging system according to the pulse sequence commands;
    providing the current dataset to the first input of the first machine learning model in combination with at least a previous dataset acquired in a previous repetition preceding the current repetition;
    receiving a prediction of a motion artifact level of the acquired magnetic resonance imaging data from the first output of the first machine learning model, the motion artifact level characterizing a number and/or extent of motion artifacts present in the acquired magnetic resonance imaging data;
    when the prediction indicates an increased number and/or extent of motion artifacts present in the acquired magnetic resonance imaging data relative to a previous prediction received in the previous repetition preceding the current repetition, checking whether omitting the current repetition results in a next prediction received in a next repetition following the current repetition that also indicates an increased number and/or extent of motion artifacts present in the acquired magnetic resonance imaging data relative to the previous prediction of the previous repetition preceding the current repetition;
    when omitting the current repetition does not result in the next prediction indicating an increased number and/or extent of motion artifacts, continuing the repeated performing of the acquisition and analysis process without the current dataset of the current repetition; and
    when omitting the current repetition does result in the next prediction indicating an increased number and/or extent of motion artifacts, continuing the repeated performing of the acquisition and analysis process with the current dataset of the current repetition.

2. The magnetic resonance imaging system of claim 1, wherein execution of the machine executable instructions further causes the processor to control the magnetic resonance imaging system to automatically abort the repeated performing of the acquisition and analysis process, when the prediction of the motion artifact level exceeds a first predefined threshold.

3. The magnetic resonance imaging system of claim 2, wherein execution of the machine executable instructions further causes the processor to control the magnetic resonance imaging system to automatically restart the repeated performing of the acquisition and analysis process when the prediction of the motion artifact level exceeds the first predefined threshold.

4. The magnetic resonance imaging system of claim 2, wherein the memory further stores a second machine learning model comprising a second deep learning network, wherein the second machine learning model comprises a second input and a second output,
wherein execution of the machine executable instructions further causes the processor to control the magnetic resonance imaging system to:
    when the prediction of the motion artifact level exceeds a second predefined threshold, provide the current dataset to the second input of the second machine learning model,
    provide a motion-artifact-corrected dataset as a replacement for the current dataset using a response received from the second output of the second machine learning model, and
    continue the repeated performing of the acquisition and analysis process with the motion-artifact-corrected dataset.

5. The magnetic resonance imaging system of claim 4, wherein the memory further stores a second learning algorithm for generating the second machine learning model, wherein execution of the machine executable instructions further causes the processor to control the magnetic resonance imaging system to:
    receive second training sets, each second training set comprising a magnetic resonance imaging dataset and a motion-artifact-only magnetic resonance imaging dataset assigned to the magnetic resonance imaging dataset, and execute the second learning algorithm on the received second training sets for generating the second machine learning model being trained with each of the second training sets to provide via the second output in response to receiving via the second input the magnetic resonance imaging dataset of a respective second training set, the motion-artifact-only magnetic resonance imaging dataset of the respective second training set enabling a providing of the motion-artifact-corrected dataset using the magnetic resonance imaging dataset provided to the second input by subtracting the motion-artifact-only magnetic resonance imaging dataset received from the second output.

6. The magnetic resonance imaging system of claim 1, wherein the prediction of the motion artifact level depends on a location of the motion artifact relative to one or more anatomical structures of interest represented by the acquired magnetic resonance imaging data.

7. The magnetic resonance imaging system of claim 1, wherein the current dataset comprises a magnetic resonance image reconstructed using the acquired magnetic resonance imaging data.

8. The magnetic resonance imaging system of claim 1, wherein the current dataset has a common predefined size as other datasets, wherein the current dataset comprises magnetic resonance imaging data from sampling points distributed over k-space with a higher sampling rate at a center of the k-space relative to an outer portion of the k-space.

9. The magnetic resonance imaging system of claim 1, wherein the current dataset has an arbitrary size being selected within a range defined by a predefined minimum size and a predetermined maximum size, wherein the current dataset comprises magnetic resonance imaging data from sampling points distributed over k-space with a higher sampling rate at a center of the k-space relative to an outer portion of the k-space.

10. The magnetic resonance imaging system of claim 1, wherein the memory further stores a first learning algorithm for generating the first machine learning model, wherein execution of the machine executable instructions further causes the processor to control the magnetic resonance imaging system to:

receive first training sets, each first training set comprising a magnetic resonance imaging dataset and an artifact level identifier identifying an artifact level assigned to the respective magnetic resonance imaging dataset, execute the first learning algorithm on the received first training sets for generating the first machine learning model.

11. A non-transitory computer readable medium storing machine executable instructions for execution by a processor controlling a magnetic resonance imaging system using pulse sequence commands and a first machine learning model comprising a first deep learning network, wherein the pulse sequence commands are configured for controlling the magnetic resonance imaging system to acquire a set of magnetic resonance imaging data, wherein the first machine learning model comprises a first input and a first output, wherein execution of the machine executable instructions causes the processor to repeatedly perform an acquisition and analysis process, wherein for each current repetition, the acquisition and analysis process comprises:

acquiring a current dataset comprising a subset of the set of magnetic resonance imaging data from an imaging zone of the magnetic resonance imaging system according to the pulse sequence commands;

providing the current dataset to the first input of the first machine learning model in combination with at least a previous dataset acquired in a previous repetition preceding the current repetition;

receiving a prediction of a motion artifact level of the acquired magnetic resonance imaging data from the first output of the first machine learning model, the motion artifact level characterizing a number and/or extent of motion artifacts present in the acquired magnetic resonance imaging data;

when the prediction indicates an increased number and/or extent of motion artifacts present in the acquired magnetic resonance imaging data relative to a previous prediction received in the previous repetition preceding the current repetition, checking whether omitting the current repetition results in a next prediction received in a next repetition following the current repetition that also indicates an increased number and/or extent of motion artifacts present in the acquired magnetic resonance imaging data relative to the previous prediction of the previous repetition preceding the current repetition;

when omitting the current repetition does not result in the next prediction indicating an increased number and/or extent of motion artifacts, continuing the repeated performing of the acquisition and analysis process without the current dataset; and when omitting the current repetition does result in the next prediction indicating an increased number and/or extent of motion artifacts, continuing the repeated performing with the current dataset.

12. The non-transitory computer readable medium of claim 11, wherein execution of the machine executable instructions further causes the processor to control the magnetic resonance imaging system to automatically abort the repeated performing of the acquisition and analysis process, when the prediction of the motion artifact level exceeds a first predefined threshold.

13. The non-transitory computer readable medium of claim 12, wherein execution of the machine executable instructions further causes the processor to control the magnetic resonance imaging system to automatically restart the repeated performing of the acquisition and analysis process when the prediction of the motion artifact level exceeds the first predefined threshold.

14. The non-transitory computer readable medium of claim 12, further storing a second machine learning model comprising a second deep learning network, wherein the second machine learning model comprises a second input and a second output, wherein execution of the machine executable instructions further causes the processor to control the magnetic resonance imaging system to:

provide the current dataset to the second input of the second machine learning model when the prediction of the motion artifact level exceeds a second predefined threshold, provide a motion-artifact-corrected dataset as a replacement for the current dataset using a response received from the second output of the second machine learning model, and continue the repeated performing of the acquisition and analysis process with the motion-artifact-corrected dataset.

15. The non-transitory computer readable medium of claim 11, wherein the prediction of the motion artifact level depends on a location of the motion artifact relative to one or more anatomical structures of interest represented by the acquired magnetic resonance imaging data.

16. The non-transitory computer readable medium of claim 11, wherein the current dataset comprises a magnetic resonance image reconstructed using the acquired magnetic resonance imaging data.

17. A method of operating a magnetic resonance imaging system, the method comprising:
provinding pulse sequence commands for controlling the magnetic resonance imaging system to acquire a set of magnetic resonance imaging data;
providing a first machine learning model comprising a first deep learning network, wherein the first machine learning model comprises a first input and a first output; and
repeatedly performing an acquisition and analysis process, wherein for each current repetition, the acquisition and analysis process comprises:
acquiring a current dataset comprising a subset of the set of magnetic resonance imaging data from an imaging zone of the magnetic resonance imaging system according to the pulse sequence commands;
providing the current dataset to the first input of the first machine learning model in combination with at least a previous dataset acquired in a previous repetition preceding the current repetition;
receiving a prediction of a motion artifact level of the acquired magnetic resonance imaging data from the first output of the first machine learning model, the motion artifact level characterizing a number and/or extent of motion artifacts present in the acquired magnetic resonance imaging data;
when the prediction indicates an increased number and/or extent of motion artifacts present in the acquired magnetic resonance imaging data relative to a previous prediction received in the previous repetition preceding the current repetition, checking whether omitting the current repetition results in a next prediction received in in a next repetition following the current repetition that also indicates an increased number and/or extent of motion artifacts present in the acquired magnetic resonance imaging data relative to the prediction of the previous repetition preceding the current repetition;
when omitting the current repetition does not result in the next prediction indicating an increased number and/or extent of motion artifacts, continuing the repeated performing of the acquisition and analysis process without the current dataset; and
when omitting the current repetition does not in the next prediction indicating an increased number and/or extent of motion artifacts, continuing the repeated performing of the acquisition and analysis process with the current dataset.

18. The method of claim 17, further comprising:
automatically aborting the repeated performing of the acquisition and analysis process when the prediction of the motion artifact level exceeds a first predefined threshold.

19. The method of claim 18, further comprising:
automatically restarting the repeated performing of the acquisition and analysis process when the prediction of the motion artifact level exceeds the first predefined threshold.

20. The method of claim 18, further comprising:
providing a second machine learning model comprising a second deep learning network, wherein the second machine learning model comprises a second input and a second output;
providing the current dataset to the second input of the second machine learning model when the prediction of the motion artifact level exceeds a second predefined threshold;
providing a motion-artifact-corrected dataset as a replacement for the current dataset using a response received from the second output of the second machine learning model; and
continuing the repeated performing of the acquisition and analysis process with the motion-artifact-corrected dataset.

* * * * *